(12) United States Patent
Weigert et al.

(10) Patent No.: US 11,427,630 B2
(45) Date of Patent: Aug. 30, 2022

(54) ANTIBODY INHIBITORS OF IL-38 AND METHODS OF USE THEREOF FOR TREATING OR REDUCING THE LIKELIHOOD OF CANCER IN A SUBJECT

(71) Applicant: Fraunhofer-Gesellschaft zur Förderung der angewandten Forschung e.V., Munich (DE)

(72) Inventors: Andreas Weigert, Hofheim am Taunus (DE); Javier Mora, San José (CR); Bernhard Brüne, Munich (DE); Mateusz Putyrski, Munich (DE); Michael John Parnham, Munich (DE); Andreas Ernst, Munich (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 126 days.

(21) Appl. No.: 16/612,723

(22) PCT Filed: May 7, 2018

(86) PCT No.: PCT/EP2018/061706
§ 371 (c)(1),
(2) Date: Nov. 11, 2019

(87) PCT Pub. No.: WO2018/206496
PCT Pub. Date: Nov. 15, 2018

(65) Prior Publication Data
US 2020/0165334 A1    May 28, 2020

(30) Foreign Application Priority Data
May 9, 2017 (EP) ..................... 17170237

(51) Int. Cl.
*C07K 16/24* (2006.01)
*A61P 35/00* (2006.01)
*A61K 9/00* (2006.01)

(52) U.S. Cl.
CPC .......... *C07K 16/244* (2013.01); *A61K 9/0053* (2013.01); *A61P 35/00* (2018.01); *C07K 2317/55* (2013.01); *C07K 2317/565* (2013.01); *C07K 2317/76* (2013.01); *C07K 2317/92* (2013.01)

(58) Field of Classification Search
CPC ............ C07K 16/244; C07K 2317/565; C07K 2317/76; A61P 35/00
See application file for complete search history.

(56) References Cited

FOREIGN PATENT DOCUMENTS

| EP | 1 366 822 A2 | 12/2003 |
|---|---|---|
| WO | WO 2000/071719 | 11/2000 |
| WO | WO03/048376 A2 | 6/2003 |
| WO | WO 2008/028115 A2 | 3/2008 |
| WO | WO 2012/177595 D8 | 12/2012 |
| WO | WO 2013/113504 A1 | 8/2013 |
| WO | WO2016/012312 A1 | 1/2016 |
| WO | WO 2016/168542 D7 | 10/2016 |
| WO | WO 2016/181171 A1 | 11/2016 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Ciccia et al., Interleukin-36 Axis is Modulated in Patients With Primary Sjogren's Syndrome, The Journal of Translational Immunology, vol. 181, pp. 230-238, 2015.
Dlugosz et al., Development of a Robotic Platform for Automated Protoplast Isolation, Transformation, and Screening of Plant Suspension Cultures, In Vitro Cellular & Developmental Biology, vol. 52, No. Suppl 1, pp. S53, 2016.
Gentles et al., The Prognostic Landscape of Genes and Infiltrating Immune Cells Across Human Cancers, Nature Medicine, vol. 21, No. 8, pp. 938-949, 2015.
Guery et al., Th17 Cell Plasticity and Functions in Cancer Immunity, BioMed Research International, vol. 2015, pp. 1-12, 2015.
Hu et al., Expression, Purification of IL-38 in *Escherichia coli* and Production of Polyclonal Antibodies, Protein Expression and Purification, vol. 107, pp. 76-82, 2015.
International Preliminary Report On Patentability, dated Dec. 3, 2019, in International Application No. PCT/EP2018/064477.
International Search Report & Written Opinion, dated Jul. 27, 2018, in International Application No. PCT/EP2018/064477.
Lin et al., Cloning and Characterization of IL-1HY2, a Novel lnterleukin-1 Family Member, The Journal of Biological Chemistry, vol. 276, No. 23, pp. 20597-20602, 2001.

(Continued)

*Primary Examiner* — Robert S Landsman
(74) *Attorney, Agent, or Firm* — Knobbe, Martens, Olson & Bear, LLP

(57) ABSTRACT

An inhibitor of IL-38 is useful for treating and/or preventing cancer in a subject. A pharmaceutical composition can include an inhibitor of IL-38. A method for treating and/or preventing cancer is carried out by administering an inhibitor of IL-38 in a therapeutically effective amount. Another method is useful for identifying an inhibitor of IL-38.

13 Claims, 7 Drawing Sheets
Specification includes a Sequence Listing.

(56) References Cited

OTHER PUBLICATIONS

Liu et al., High-throughput transformation of *Saccharomyces cerevisiae* using liquid handling robots, Plos One, vol. 12, No. 3, pp. e0174128, 2017.

Mora et al., Interleukin-38 is Released form apoptotic Cells to Limit Inflammatory Macrophage Response, Journal of Molecular Cell Biology, vol. 8, No. 5, pp. 426-438, 2016.

Nussbaumer et al., Essential Requirements of Zoledronate-Induced Cytokine and gd T Cell Proliferative Responses, Journal of Immunology, vol. 191, pp. 1346-1355, 2013.

Scioli et al., Cloning and Characterization of a cDNA Encoding the Chloroplastic Copper/Zinc-Superoxide Dismutase From Pea, Proceedings of the National Academy of Sciences of the United States of America, vol. 85, pp. 7661-7665, 1988.

Silva-Santos et al., γδ T Cells in Cancer, Nature Reviews Immunology, vol. 15, pp. 683-691, 2015.

Sutton et al., Interleukin-1 and IL-23 Induce Innate IL-17 Production from gd T Cells, Amplifying Th17 Responses and Autoimmunity, Immunity, vol. 31, pp. 301-341, 2009.

Takada et al., Clinical Implications of the Novel Cytokine IL-38 Expressed in Lung Adenocarcinoma: Possible Association with PD-L1 Expression, Polsone, vol. 12, No. 7, pp. 1-15, 2017.

Van De Veerdonk et al., IL-38 Binds to the IL-36 Receptor and has Biological Effects on Immune Cells Similar to IL-36, Receptor Antagonist, PNAS, vol. 109, No. 8, pp. 3001-3005, 2012.

Yuan et al., Production of Recombinant Human Interleukin-38 and It's Inhibitory Effect on the Expression of Proinflammatory Cytokines in THP-1 Cells, Molecular Cell Biology, vol. 50, No. 3, pp. 466-473, 2016.

Zhu et al., Accurate In Vitro Transcription From Circularized Plasmid Templates by Plant Whole Cell Extracts, The Plant Journal, Blackwell Scientific Publications, vol. 7, No. 6, pp. 1021-1030, 1995.

Communication pursuant to Article 94(3) EPC dated May 19, 2022 in EP Patent Application No. 18 722 989.3.

* cited by examiner

Figure 1
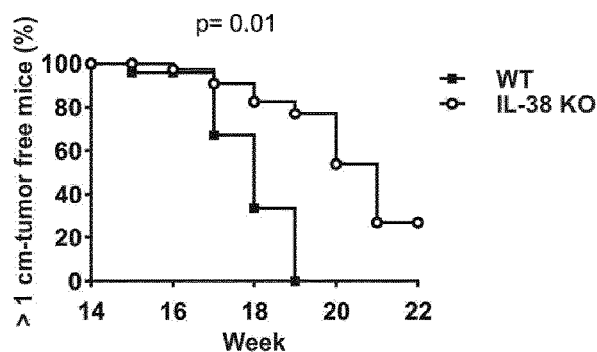
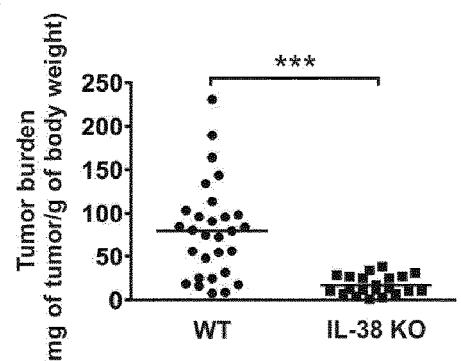
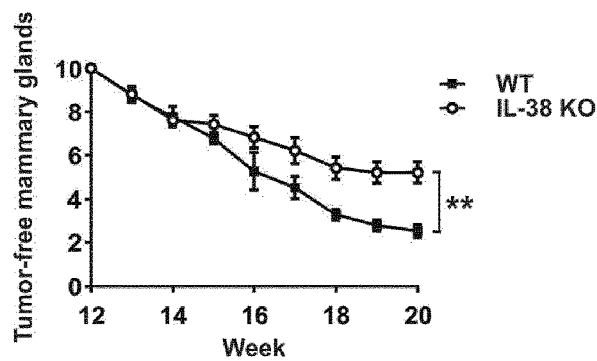
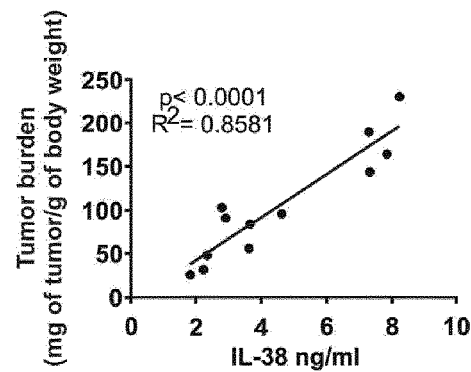

Figure 5
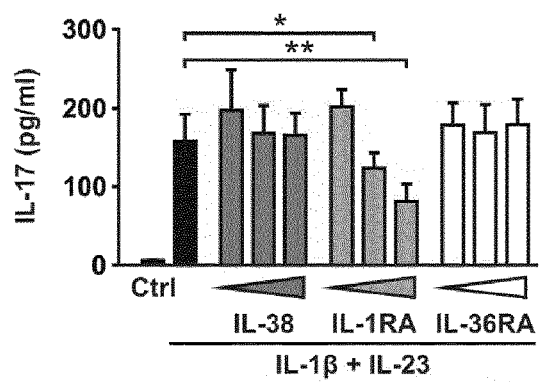
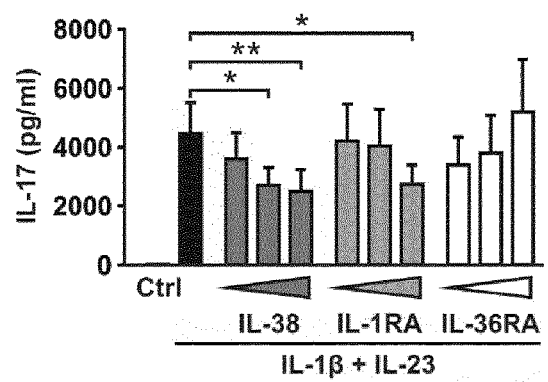
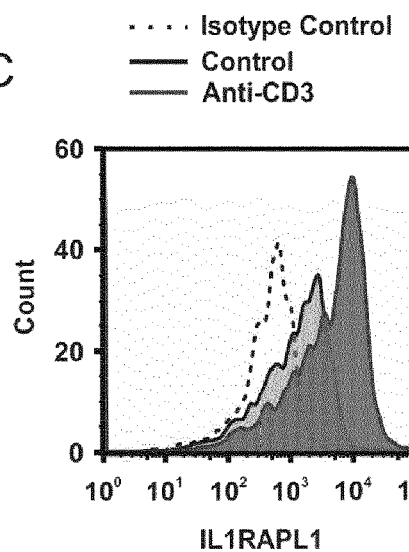

Figure 6

Fab e04 light chain variable:

```
            FR1                    CDR1              FR2                CDR2              FR3                                    CDR3                  FR4
          (1-26)                  (27-38)          (39-55)             (56-65)          (66-104)                              (105-117)             (118-127)
     1          10          20          30          40          50          60          70          80          90         100         110         120
     |....|....|....|....|....|....|....|....|....|....|....|....|....|....|....|....|....|....|....|....|....|....|....|....|....|
     DIQMTQSPSSLSASVGDRVTITCRAS QSV......YH VAWYQQKPGKAPKLLIY SA........ SLYSGVP.SRFSGSR..SGTDFTLTISSLQPEDFATYYC QQVF....APIT FGQGTKVEIK  (SEQ ID NO: 1)
```

Fab e04 heavy chain variable:

```
            FR1                    CDR1              FR2                CDR2              FR3                                    CDR3                  FR4
          (1-26)                  (27-38)          (39-55)             (56-65)          (66-104)                              (105-117)             (118-128)
     1          10          20          30          40          50          60          70          80          90         100         110         120
     |....|....|....|....|....|....|....|....|....|....|....|....|....|....|....|....|....|....|....|....|....|....|....|....|....|....|
     EVQLVESGG.GLVQPGGSLRLSCAASGFSF....SSGS IHWVRQAPGKGLEWVAS IBFI..HSYT SYADSVK.GRFTISADTSKNTAYLQMNSLRAEDTAVYYC ARTVRSSRPAYEGWAMDY WGQGTLVTVSS  (SEQ ID NO: 2)
```

Fab h06 light chain variable:

```
            FR1                    CDR1              FR2                CDR2              FR3                                    CDR3                  FR4
          (1-26)                  (27-38)          (39-55)             (56-65)          (66-104)                              (105-117)             (118-127)
     1          10          20          30          40          50          60          70          80          90         100         110         120
     |....|....|....|....|....|....|....|....|....|....|....|....|....|....|....|....|....|....|....|....|....|....|....|....|....|....|
     DIQMTQSPSSLSASVGDRVTITCRAS QSV......SYSH VAWYQQKPGKAPKLLIY SA........ SLYSGVP.SRFSGSR..SGTDFTLTISSLQPEDFATYYC QQAYM...SPIT FGQGTKVEIK  (SEQ ID NO: 3)
```

Fab h06 heavy chain variable:

```
            FR1                    CDR1              FR2                CDR2              FR3                                    CDR3                  FR4
          (1-26)                  (27-38)          (39-55)             (56-65)          (66-104)                              (105-117)             (118-128)
     1          10          20          30          40          50          60          70          80          90         100         110         120
     |....|....|....|....|....|....|....|....|....|....|....|....|....|....|....|....|....|....|....|....|....|....|....|....|....|....|
     EVQLVESGG.GLVQPGGSLRLSCAASGFSI....SYSH IHWVRQAPGKGLEWVAS ISFS..HSYT SYADSVK.GRFTISADTSKNTAYLQMNSLRAEDTAVYYC ARAPVEHVWPLSGEDY WGQGTLVTVSS  (SEQ ID NO: 4)
```

ANTIBODY INHIBITORS OF IL-38 AND METHODS OF USE THEREOF FOR TREATING OR REDUCING THE LIKELIHOOD OF CANCER IN A SUBJECT

PRIORITY AND CROSS REFERENCE TO RELATED APPLICATIONS

This application is the U.S. National Phase Application under 35 U.S.C. § 371 of International Application No. PCT/EP2018/061706, filed May 7, 2018, designating the U.S. and published in English as WO 2018/206496 A1 on Nov. 15, 2018, which claims the benefit of European Application No. EP 17170237.6, filed May 9, 2017. Any and all applications for which a foreign or a domestic priority is claimed is/are identified in the Application Data Sheet filed herewith and is/are hereby incorporated by reference in their entireties under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled HRZG001003APCSEQLIST.txt, created and last saved on Nov. 7, 2019, which is 11,167 bytes in size. The information in the Electronic Sequence Listing is incorporated herein by reference in its entirety.

FIELD

The present invention relates to inhibitors of IL-38 for use in treating and/or preventing cancer in a subject.

SUMMARY

The present invention relates to an inhibitor of IL-38 for use in treating and/or preventing cancer in a subject. Also encompassed by the invention are a pharmaceutical composition comprising an inhibitor of IL-38, a method for treating and/or preventing cancer comprising administering an inhibitor of IL-38 in a therapeutically effective amount as well as a method for identifying an inhibitor of IL-38.

BRIEF DESCRIPTION OF THE DRAWINGS

FIG. 1 shows IL-38-deficiency impairs PyMT tumor growth. (A) Tumor diameter and (B) tumor free glands were measured in wildtype (WT) and IL-38 knockout mice (IL-38 KO) in a polyoma middle T oncoprotein (PyMT) mammary carcinoma background (n=22). Data are means±SEM. (C) At week 18 tumors were extracted to calculate the tumor burden in terms of the mice body weight (n=30). (D) The intratumoral levels of IL-38 were measured using Cytometric bead array, and its concentration was correlated with the tumor burden of WT mice n=12. p-values were calculated using (A) Chi square, (B, C) Student's t-test and (D) linear regression.  $p<0.01$, * $p<0.001$.

FIG. 5 shows IL-38 directly blocks γδ T cell IL-17 production after TCR stimulus, which increases IL1RAPL1 surface expression. γδ T cells were isolated from spleens and seeded on (A) uncoated and (B) anti-CD3 antibody coated plates. After stimulation with IL-1β (10 ng/ml) and IL-23 (10 ng/ml) in combination with different concentrations (10 ng/ml, 50 ng/ml, 100 ng/ml) of either IL-38, IL-1RA and IL-36RA, IL-17 concentration was measured using Cytometric Beads Array n=10. (C) Representative FACS histogram of the surface expression of IL-1RAPL1 after TCR stimulus (of 6 independent experiments). Data are means±SEM. p-values were calculated using Student's t-test. * $p<0.05$, ** $p<0.01$.

FIG. 6 shows amino acid sequences of the variable chains of Fab E04 and H06. Determination of FR (framework region) and CDR (complementarity-determining region) boundaries (given in brackets) and amino acid numbering according to IMGT scheme (www.imgt.org). Asterisks denote additional amino acids in CDR3 of heavy chains. In case of Fab E04 these are positions 111.1, 111.2, 111.3, 112.3, 112.2 and 112.1. In case of Fab H06 these are positions 111.1, 112.2 and 112.1.

DETAILED DESCRIPTION

Figure 2:
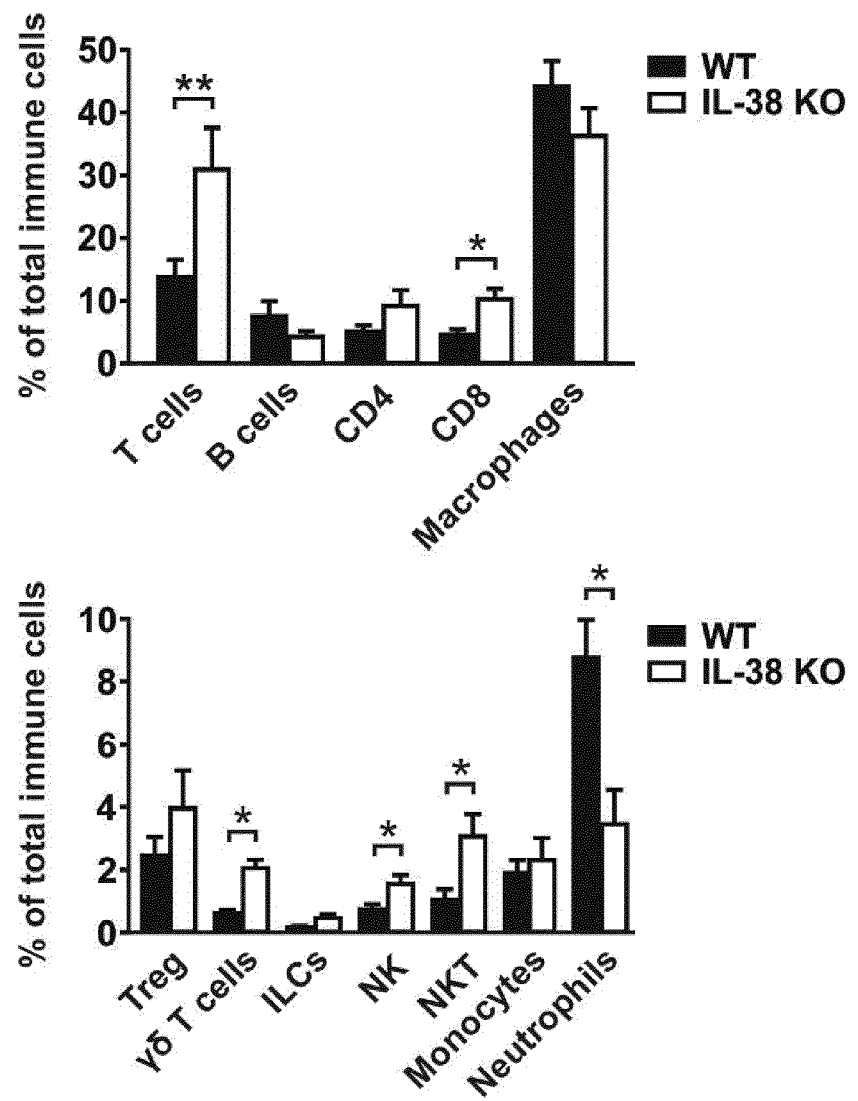
FIG. 2 shows increased percentage of pro-inflammatory and anti-tumoral cell populations in IL-38 KO PyMT tumors. At week 18 PyMT tumors were extracted from wildtype (WT) and IL-38 knockout (IL-38 KO) mice and the immune cell infiltration was determined using multicolor flow cytometry (n=10). Data are means±SEM. p-values were calculated using Student's t-test. * $p<0.05$, ** $p<0.01$.

Cancer is still one of the leading causes of death in our society. Thus, the development of effective agents for the prevention and treatment of cancer is of high importance. Classical tumor therapies, such as radiation therapy and chemotherapy, are known to have a variety of drawbacks, for example difficult administration and unwanted side effects. Moreover, the right dosage of radiation or chemotherapeutic agents is often difficult. In case the dose is too low, it will be ineffective against the tumor, whereas, if the dose is too high, the toxicity and the caused side-effects may be intolerable to the patient.

In the past few years, targeted therapies as well as the activation of the body's own immune system to fight cancer came into focus. Especially, cancer immuno-therapy became a high priority in scientific research and therapeutic applications. On the one hand, active immunotherapeutic approaches are pursued that are directed against tumor-associated antigens (TAAs). TAAs are often expressed on the surface of cancer cell, and thus can be recognized by immune cells such as cytotoxic T cells or natural killer (NK) cells. Activation of the immune system may be achieved by administering immuno-stimulatory molecules such as interleukin-12 or type 1 interferons. However, the therapeutic efficacy of these molecules has been shown to be limited which is mainly due to feedback responses such as the up-regulation of immune checkpoints. On the other hand, passive immuno-therapeutic approaches aim to enhance existing anti-tumor responses, for example by inhibiting regulatory T cells. As passive agents, interleukin-2 and interferon-α were shown to enhance anti-tumor activity and have been approved for use in the treatment of certain advanced cancers, i.e. malignant melanoma.

Previous studies on cancer drugs and their effect on the immune system mainly focused on chemotherapeutic agents, that, in addition to a cytotoxic effect on tumor cells, could also activate the immune system. Moreover, inhibitors of immunosuppressive surface molecules, so-called immune checkpoints, were shown to improve patient survival. For example, the neutralization of Programmed cell death protein 1 (PD-1) was shown to reactivate the body's own immune system, significantly improving patient survival in metastatic melanoma and non-small cell lung carcinoma compared to conventional therapy. However, immunogenic chemotherapy and blockade of immune checkpoints such as the anti-PD-1 therapy is not effective in all patients and resistances may be acquired due to activation of alternative immuno-suppressive signaling pathways. In addition, blockade of immune checkpoints is often accompanied by autoimmune side effects and thus, new target structures for reactivation of the body's own immune system against tumors are needed.

Moreover, specific cellular and molecular immune signatures were shown to indicate a good or a poor prognosis for the survival of tumor patients. An infiltration of cytotoxic and proinflammatory lymphocyte populations such as γδ-T cells, cytotoxic CD8$^+$ T cells, natural killer (NK) cells or TH1-polarized CD4$^+$ T cells into the tumor has been reported to be associated with a good prognosis, while the infiltration of anti-inflammatory or tolerogenic immune cells such as macrophages, myeloid-derived suppressor cells or regulatory T cells was associated with a poor prognosis (Gentles et al., 2015, The prognostic landscape of genes and infiltrating immune cells across human cancers. Nature medicine 21.8: 938-945). Thus, therapeutic agents, that are able to both activate the infiltration of cytotoxic and pro-inflammatory immune cells and at the same time to reactivate or deplete immunosuppressive immune cells are needed.

Cytokines are molecular messengers that allow communication between cells of the immune system and thus, can coordinate a response to an immunogen, i.e. a tumor associated antigen (TAA). Especially at the tumor site, certain cytokines were shown to stimulate immune effector cells and enhance tumor cell recognition by cytotoxic effector cells such as CD8$^+$ T cells. In the past few years, several cytokines have entered clinical trials for patients with advanced cancer including GM-CSF, IL-7, IL-12, IL-15, IL-18 and IL-21. These cytokines supposedly directly activate CD8+ effector T cells or lead to an expansion of CD8+ effector T cell populations over CD4$^+$FOXP3$^+$ regulatory T cells.

Cytokines of the IL-1 family, such as IL-1, IL-33 or IL-36, were also shown to have an immuno-stimulatory effect in tumors, whereas their receptor antagonists can promote tumor growth. Interleukin 38 (IL-38), also referred to as IL1F10 and IL-1HY2, is a new, largely uncharacterized member of the IL-1 family IL-38 has been shown to be primarily expressed in the skin and lymphoid tissues in humans and mice, and has been suggested to play a role in immunological processes (Lin et al., 2001, Cloning and characterization of IL-1HY2, a novel interleukin-1 family member. Journal of Biological Chemistry 276.23: 20597-20602.). IL-38 shares about 41% homology with the IL-1 receptor antagonist (IL-1RN) and 43% homology with IL-36RN (Mora et al., 2016, Interleukin-38 is released from apoptotic cells to limit inflammatory macrophage responses, J Mol Cell Biol 8: 426-438.). IL-38 polymorphisms have been associated with an increased tendency to develop autoimmune diseases such as Bechterew's disease, rheumatoid arthritis or psoriasis arthritis. Autoimmune diseases are usually associated with the activation of pro-inflammatory cells such as TH1 or TH17 cells and/or cytotoxic immune cell populations. It has recently been shown that IL-38 can actually inhibit the manifestation of a TH17 immune response which may be explained by the antagonizing effect of IL-38 on the IL-36 receptor (IL1R6) as well as on the IL-1 family orphan receptor IL-1 receptor fragment protein-like 1 (IL1RAPL1) (van de Veerdonk et al., 2012, IL-38 binds to the IL-36 receptor and has biological effects on immune cells similar to IL-36 receptor antagonist. Proceedings of the National Academy of Sciences 109.8: 3001-3005). However, so far, IL-38 has not been implicated to play a role in cancer immunology.

WO2016/012312 discloses a truncated version of IL-38 which has anti-inflammatory activities and may be used to treat immune or inflammatory diseases such as septic shock, hemorrhagic shock, arthritis, for example spondyloarthritis, rheumatoid arthritis, psoriatic arthritis or osteoarthritis, inflammatory bowel disease, multiple sclerosis and metabolic diseases such as arteriosclerosis and type I diabetes.

Although several immuno-therapeutic agents have entered clinical trials or are already approved in patients with advanced cancer, the current immuno-therapeutic approaches have the drawback that treatment is not effective in all patients and that treatment-acquired resistance often quickly arises. In most cases, the latter is due to the activation of compensatory immune-suppressive pathways. Thus, therapeutic agents that have a broader effect on the immune system and, for example, can both activate the infiltration of cytotoxic and pro-inflammatory immune cells at the tumor site and at the same time reactivate or deplete immunosuppressive immune cells would be very beneficial for tumor treatment.

In view of the above, an ongoing demand exists for the development of immuno-therapeutic agents for use in the prevention and/or treatment of cancer.

The technical problem underlying the present invention can be seen as the provision of means and methods for complying with the aforementioned needs. The technical problem is solved by the embodiments characterized in the claims and herein below.

The present invention pertains to an inhibitor of IL-38 for use in treating and/or preventing cancer in a subject.

The term "IL-38" or "interleukin-38" refers to a member of the interleukin 1 (IL-1) family, also known as IL1F10 or IL-1HY2. The IL-1 family currently comprises 11 cytokines, namely IL-1α, IL-1β, IL-1Ra, IL-18, IL-36Ra, IL-36a, IL-37, IL-36β, IL-36γ, IL-33 and IL-38. IL-38 and further members of the IL family are known to those skilled in the art. Moreover, nucleic acid as well as protein sequences can be found in standard databases such as NCBI Gene or UniProtKB. Preferably, the protein sequence of human IL-38 can be found in the UniProtKB database under the accession number Q8WWZ1, while the protein sequence of mouse IL-38 can be found under the accession number Q8R459.

In addition to the aforementioned specific sequences for human or mouse IL-38, the term IL-38 as used herein also encompasses variants of IL-38 proteins having said specific sequences. A variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific IL-38 proteins mentioned above. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman, by the homology alignment algorithm of Needleman and Wunsch, by the search for similarity method of Pearson and Lipman, by computerized implementations of these algorithms GAP, BESTFIT, BLAST, PASTA, and TFASTA in the Wisconsin Genetics Software Package, Genetics Computer Group (GCG), 575 Science Dr., Madison, Wis., or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologues. Moreover, the variants referred to herein include fragments of the specific IL-38 proteins or the aforementioned types of variants as long as these fragments have the essential immunological and biological properties as referred to above. Such fragments may be, e.g., degradation products or splice variants of the IL-38 proteins. Further included are variants which differ due to posttranslational modifications.

Members of the IL-1 family of cytokines such as IL-38 typically bind to receptors of the IL-1 family that are characterized by extracellular immunoglobulin(-like) domains and an intracellular signal transduction domain, the so-called Toll/Interleukin-1R (TIR) domain. Cytokines of the IL-1 family may bind to the same or to different receptors. For example, both IL-1α and IL-1β were shown to bind to the same receptor molecule, namely IL-1RI. However, also a third ligand of this receptor exists, termed Interleukin 1 receptor antagonist (IL-1Ra), which does not activate downstream signaling. IL-1Ra instead acts as an inhibitor of IL-1α and IL-1β signaling by competing with them for binding sites of the receptor IL-1RI. IL-38 was suggested to have an antagonizing effect on the on the IL1R6, also known as IL-36 receptor, as well as on the orphan receptor IL1RAPL1 (IL-1 receptor accessory protein-like 1). Current members of the interleukin-1 receptor (IL-1R) family include IL-1R1 (IL-1RI), IL-1R4 (ST2), IL-1R5 (IL-18R), IL-1R6 (IL-1Rrp2), IL-1R3 (IL-1RAcP), IL-1R7 (IL-18AcP), IL-1R2 (IL-1RII), TIR-8 (SIGIRR), IL-1RAPL2 (TIGIRR-1) and IL-1RAPL1 (TIGIRR-2). However, the specific receptors and co-receptors for the all members of the IL-1 family of cytokines have not been described in detail or are currently unknown. It is understood by those skilled in the art that further members of the IL-1 and/or the IL-1 receptor family and their mode of action, i.e. the activation of specific signal pathways, may be identified in the future.

IL-38 has been suggested to play a role in immunological processes. However, its functional role is still largely unknown. IL-38 was shown to be primarily expressed in the skin and lymphoid tissues in humans and mice and supposedly affect immunological processes. IL-38 shares about 41% homology with the IL-1 receptor antagonist (IL-1RN) and 43% homology with IL-36RN. IL-38 was recently shown to bind to the IL-36 receptor, thereby having an antagonizing effect on the IL-36 receptor, similar to IL-36Ra. IL-38 was also reported to exert an antagonizing effect on IL1RAPL1. IL-38 was further shown to be released from apoptotic cells to limit inflammatory macrophage responses. Moreover, IL-38 polymorphisms have been associated with an increased tendency to develop autoimmune diseases such as Bechterew's disease, rheumatoid arthritis or psoriasis arthritis. It is known to those skilled in the art that autoimmune diseases are often associated with the activation of pro-inflammatory cells such as TH1 or TH17 cells and/or cytotoxic immune cell populations. It has recently been shown that IL-38 can actually inhibit the manifestation of a TH17 immune response which may be explained by the antagonizing effect of IL-38 on the IL-36 receptor (IL1R6) as well as on the orphan receptor IL-1 receptor accessory protein-like 1 (IL1RAPL1).

The "IL-1 receptor accessory protein-like 1" or "IL1RAPL1" as used herein refers to an orphan receptor also known as TIGIRR-2, which was originally referred to as IL-1R8. Nucleic acid as well as protein sequences of IL1RAPL1 can be found in standard databases such as NCBI Gene or UniProtKB. For example, the protein sequence of human IL1RAPL1 can be found in the UniProtKB database under the accession number Q9NZN1, while the protein sequence of mouse IL1RAPL1 can be found under the accession number P59823. The protein encoded by the IL1RAPL1 has been characterized as a member of the interleukin-1 receptor family and is closely related to IL1RAPL2 (TIGIRR-2). IL1RAPL1 has been associated with X-linked non-syndromic mental retardation and mutations or deletions in the IL1RAPL1 gene were found in patients with mental retardation. The downstream signaling cascade starting from IL1RAPL1 has not been fully described, but activation of c-Jun N-terminal protein kinase (JNK) has been suggested. According to the present invention, IL1RAPL1 is preferably expressed on γδ-T cells as explained in detail elsewhere herein.

The term "inhibitor of IL-38" as used herein refers to any substance that is capable of reducing, partially impairing and/or fully inhibiting the activity of IL-38. It will be understood that IL-38 activity refers to the capability of IL-38 to activate or suppress downstream signaling molecules. Preferably, an inhibitor of IL-38 inhibits the binding of IL-38 to a receptor, preferably the IL-36 receptor (IL1R6) and/or IL1RAPL1, thereby preventing the antagonizing effect of IL-38 on these receptors. Known agonists of receptors of the IL-1 family, e.g., the agonists IL36A and IL36B, which bind to and activate the IL-36 receptor, typically lead to the activation of downstream signaling pathways which further induce pro-inflammatory mediators, such as NF-κB and mitogen-activated protein kinases (MAPKs). These pro-inflammatory mediators further stimulate an immune response, for example by activating T cell proliferation and release of IL-2. On the contrary, receptor antagonists of the IL-36 receptor such as IL36Ra and IL-38 inhibit activation of downstream signaling and thus block the induction of a pro-inflammatory response. An inhibitor of IL-38 according to the present invention preferably releases said antagonistic effect of IL-38 blockage on the IL-36 receptor (IL1R6) and/or the IL-1 receptor accessory protein-like 1 (IL1RAPL1).

It will be understood by those skilled in the art that an inhibitor of IL-38 may act as a direct or indirect inhibitor molecule. Such a direct inhibitor can be reversible or non-reversible bound to IL-38. For example, direct inhibition of IL-38 can be achieved by directly interacting with and thereby inhibiting the activity of the IL-38 protein, for example by an antibody that, once bound to IL-38, blocks its activity. As a result, binding of IL-38 to the IL-36 receptor (IL1R6) and/or the IL-1 receptor accessory protein-like 1 (IL1RAPL1) is not possible any more. Indirect inhibition, for example, can be achieved by inhibition of an IL-38-activating molecule and/or by allosteric inhibition. For example, an allosteric inhibitor can be molecule that binds to a different site at a receptor for IL-38 and thus, prevents binding of IL-38 to said receptor. It will be further understood by those skilled in the art that inhibition of IL-38 activity can take place at the DNA, RNA or protein level. For example, said inhibition can be achieved by decreasing the expression of the DNA, RNA and/or protein. For example, inhibitors of IL-38 can be molecules that lead to tight packaging of DNA or are transcriptional inhibitors, respectively, so that IL-38 mRNA cannot be made. Inhibitors of IL-38 also include post-transcriptional inhibitors which accomplish that the IL-38 protein is not correctly translated or transported and thus, does not function properly. It is further known by those skilled in the art that gene-therapeutic approaches such as the use of specific Zinc-Finger Nucleases, TALEN or CRISPR constructs can also result in inhibition of IL-38. For example, a CRISPR-Cas9 construct targeting IL-38 that leads to deletion of part of or the whole IL-38 gene can be seen as an inhibitor of IL-38. In case, the IL-38 gene is deleted, a functional mRNA and thus a functional protein cannot be made. Preferably, gene-therapeutic approaches such as CRISPR-Cas9 will be performed in vitro on selected cells from the subject. Multiple cell types may produce IL-38 upon induction of apoptotic cell death. For example, such cells may be isolated from a subject, subjected to CRISPR-Cas9 therapy targeting IL-38 and further cultured in vitro with or without induction of cell death. Moreover, naturally IL-38-producing cells such as B-cells may be isolated from a blood sample of a subject, subjected to CRISPR-Cas9 therapy targeting IL-38 and further cultured in vitro. The cells lacking the IL-38 gene may then be given back to the subject, i.e. by injection, so that these cells are not able to produce IL-38 anymore.

Preferably, said inhibitor of IL-38 for use according to the present invention is a direct inhibitor of IL-38. More preferably, said inhibitor of IL-38 is a peptide or protein, a ribozyme, an antibody, a small molecule, a lipid, an inhibitory RNA molecule, an antisense oligonucleotide or a morpholino. Most preferably, said inhibitor of IL-38 for use according to the present invention is an antibody or a small molecule.

Preferably said inhibitor of IL-38, most preferably an antibody or a small molecule, shall specifically bind to IL-38. What is meant by specific binding is known to those skilled in the art. In essence, it means that an inhibitory agent of IL-38, such as an antagonistic antibody, should not substantially bind to, i.e. "cross-react" with, another peptide, polypeptide or substance. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance. Binding of the binding agent can be measured by any method known in the art. Preferably, said method is semi-quantitative or quantitative.

A "peptide or protein" as referred to herein relates to a molecule consisting of amino-acid residues joined by peptide bonds. Peptides, consisting of several, typically, at least 20, at least 30, at least 40, at least 50 or at least 60 amino acids that are covalently linked to each other by peptide bonds, are commonly referred to as polypeptides. Molecules consisting less than 20 amino acids covalently linked by peptide bonds are typically considered to be peptides. In a preferred embodiment, the peptide or protein shall be a direct or indirect inhibitor of IL-38. More preferably, the peptide or protein shall directly bind to IL-38, thereby inhibiting its activity, for example its activity of binding to and blocking pro-inflammatory downstream signaling of the IL-36 receptor (IL1R6) and/or the IL-1 receptor accessory protein-like 1 (IL1RAPL1). Furthermore, a truncated variant of IL-38 protein may be used. Preferably, the truncated variant of IL-38 is the truncated IL-38 protein disclosed in WO2016/012312.

The term "ribozyme" as used herein relates to an RNA molecule that is capable of catalyzing specific biochemical reactions, including cleavage and/or ligation of RNA and DNA and peptide bond formation. Methods of designing and constructing ribozymes are known in the art and include, for example, de novo rational design, oligonucleotide synthesis and in vitro-transcription. It is also known in the art that ribozymes can be stably integrated or transiently introduced into cells as part of a recombinant DNA construct such as a plasmid or vector. It will be understood that such a DNA construct may contain additional regulatory elements such as an enhancer, a constitutive or inducible promoter or a terminator. The ribozyme shall be a direct or indirect inhibitor of IL-38. In a preferred embodiment, the ribozyme specifically targets the IL-38 mRNA which is transcribed from the gene encoding IL-38, followed by endonucleolytic cleavage of the IL-38 mRNA. As a result, no functional IL-38 protein can be made from said cleaved mRNA and the activity of IL-38 is therefore inhibited.

The term "antibody" as used herein, also referred to as immunoglobulin, includes both polyclonal and monoclonal antibodies, as well as fragments thereof, such as Fv, Fab and F(ab)2 fragments that are capable of binding an antigen or hapten or a chemically modified derivative of any of these antibodies. Preferably, said antibody is a monoclonal antibody, more preferably a monoclonal antibody fragment, e.g. a monoclonal Fab fragment. It is known to those skilled in the art that monoclonal antibodies typically can have monovalent affinity, i.e. they bind to the same epitope (the part of an antigen that is recognized by the antibody). A Fab fragment is typically composed of one constant and one variable domain of each of the heavy chain and the light chain and can be generated by methods well known in the art including, for example, recombinant expression or cleavage of an immunoglobulin monomer into two Fab fragments and an Fc fragment using the enzyme papain. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Chemical modifications of antibodies are also known to those skilled in the art and include, for example, the coupling of an antibody to a detectable marker such as an radioactive isotope (e.g., radioactive isotopes of Iodide Technetium), fluorescent or chemoluminescent agents (e.g., FITC, rhodamin), an enzyme which is capable of generating a detectable signal by converting a substrate (e.g., horseradish peroxidase, firefly luciferase, or beta galactosidase) or a fluorescent protein (e.g., green-, blue- or red-fluorescent protein). Dependent on the type of detectable marker, different detection methods can be applied, for example, using a reader system for the signal generated by the detectable marker. Such systems include automatic signal reader device, such as an ELISA or RIA reader, but also microscopic device for manual or automatic detection of the detectable signal. In accordance with the present invention, the antibody preferably inhibits the activity of IL-38, for example by direct binding to IL-38 itself or by indirect interaction with IL-38 such as allosteric inhibition. In a preferred embodiment, the antibody is an antagonistic antibody specifically binding to IL-38 and thereby inhibiting IL-38 activity. Preferably, the antagonistic antibody binds to an epitope on IL-38 that inhibits interaction of IL-38 with the IL-36 receptor (IL1R6/) and/or IL1RAPL1.

In a preferred embodiment of the present invention said antibody is an antagonistic or neutralizing antibody, preferably an IL-38 neutralizing Fab fragment. Preferably, said IL-38 neutralizing Fab fragment binds to an epitope on IL-38 that inhibits interaction of IL-38 with the IL-36 receptor (IL1R6/) and/or IL1RAPL1. More preferably, the IL-38 neutralizing Fab fragment binds with high affinity to IL-38, most preferably to murine IL-38.

The term "affinity" refers to the strength with which an antibody molecule binds an epitope. Means and methods to determine the affinity of an antibody are well known in the art and include, for example, equilibrium dialysis and the determination of the equilibrium dissociation constant (Kd). The equilibrium dissociation constant or Kd is a ratio of Koff (indicating how quickly the antibody dissociates from its antigen) and Kon (indicating how quickly the antibody binds to its antigen). Thus, Kd and affinity are inversely related. Most antibodies have Kd values in the low micromolar ($10^{-6}$) to nanomolar ($10^{-7}$ to $10^{-9}$) range.

Typically, high affinity antibodies are considered to be in the nanomolar range ($10^{-9}$). Preferably, the Kd value of antibody is determined by Biolayer interferometry (BLI). Biolayer interferometry (BLI) as referred to herein is a simple, optical dip-and-read system that can be used for measuring interactions between proteins, peptides, nucleic acids, small molecules, and/or lipids in real time. A quantitative set of equilibrium binding affinities (K(d)) and rates of association and dissociation (k(a)/k(d)) can be measured in minutes using nanomole quantities of sample. It is well known in the art by which tests the Kd can be determined, including, for example, the Langmuir 1:1 binding model.

In a preferred embodiment of the present invention, said antibody or IL-38 neutralizing Fab fragment, has a Kd value of less than about 300 nM, less than about 200 nM or less than about 100 nM. More preferably, said Kd value is between about 5 nM and 75 nM, most preferably said KD value is a value between about 7 nM and about 70 nM.

About as referred to herein refers to any specific value referred to in this specification, e.g. the Kd value of an antibody, including any variation which is within the range of +/−20%, +/−10%, +/−5%, +/−4%, +/−3%, +/−2% or +/−1%.

In a further preferred embodiment of the present invention, said antibody or IL-38 neutralizing Fab fragment comprises the following complementarity determining regions (CDRs): a light chain CDR1 sequence comprising the amino acid sequence "QSYYSY" (E04 lc CDR1, according to SEQ ID NO. 5), a light chain CDR2 sequence comprising the amino acid sequence "SAS" (E04 lc CDR2), a light chain CDR3 sequence comprising the amino acid sequence "QQVFAPIT" (E04 lc CDR3, according to SEQ ID NO. 6), a heavy chain CDR1 sequence comprising the amino acid sequence "GFSFSSSS" (E04 hc CDR1, according to SEQ ID NO. 7) a heavy chain CDR2 sequence comprising the amino acid sequence "ISPYYSYT" (E04 hc CDR2, according to SEQ ID NO. 8) and a heavy chain CDR3 sequence comprising the amino acid sequence "ARTVRGSKKPYFSGWAMDY" (E04 hc CDR3, according to SEQ ID NO. 9). In yet a preferred embodiment of the present invention, said antibody or IL-38 neutralizing Fab fragment comprises the following complementarity determining regions (CDRs): a light chain CDR1 sequence comprising the amino acid sequence "QSVSSA" (H06 lc CDR1, according to SEQ ID NO. 10), a light chain CDR2 sequence comprising the amino acid sequence "SAS" (H06 lc CDR2), a light chain CDR3 sequence comprising the amino acid sequence "QQAYWSPIT" (H06 lc CDR3, according to SEQ ID NO. 11), a heavy chain CDR1 sequence comprising the amino acid sequence "GFSL-SYSY" (H06 hc CDR1, according to SEQ ID NO. 12), a heavy chain CDR1 sequence comprising the amino acid sequence "ISPSYSYT" (H06 hc CDR2, according to SEQ ID NO. 13) and a heavy chain CDR3 sequence comprising the amino acid sequence "ARAPVPHVWPYSGFDY" (H06 hc CDR3, according to SEQ ID NO. 14). Preferred amino acid sequences of the variable chains of the antibody fragments can also be found in Table 1 below. Moreover, the above mentioned CDRs annotated according to the IMGT-ONTOLOGY (see Giudicelli and Lefranc 1999, Bioinformatics 15:1047-1054) are shown in FIG. 6.

In a further preferred embodiment of the present invention, said antibody or IL-38 neutralizing Fab fragment comprises the following framework regions (FRs): a light chain framework region FR1 comprising the amino acid sequence "DIQMTQSPSSLSASVGDRVTITCRAS" (E04 lc FR1, according to SEQ ID NO. 15), a light chain framework region FR2 comprising the amino acid sequence "VAWYQQKPGKAPKLLIY" (E04 lc FR2, according to SEQ ID NO. 16), a light chain framework region FR3 comprising the amino acid sequence "SLYSGVPSRFSGSRSGTDFTLTISSLQPEDFATYYC" (E04 lc FR3, according to SEQ ID NO. 17), a light chain framework region FR4 comprising the amino acid sequence "FGQGTKVEIK" (E04 lc FR4, according to SEQ ID NO. 18), a heavy chain framework region FR1 comprising the amino acid sequence "EVQLVESGGGLVQPGGSLRLS- CAAS" (E04 hc FR1, according to SEQ ID NO. 19), a heavy chain framework region FR2 comprising the amino acid sequence "IHWVRQAPGKGLEWVAS" (E04 hc FR2, according to SEQ ID NO. 20), a heavy chain framework region FR3 comprising the amino acid sequence "SYADSVKGRFTISADTSKNTAYLQMNSLRAED-TAVYYC" (E04 hc FR3, according to SEQ ID NO. 21) and a heavy chain framework region FR4 comprising the amino acid sequence "WGQGTLVTVSS" (E04 hc FR4, according to SEQ ID NO. 22). In yet a preferred embodiment of the present invention, said antibody or IL-38 neutralizing Fab fragment comprises the following framework regions (FRs): a light chain framework region FR1 comprising the amino acid sequence "DIQMTQSPSSLSASVGDRVTITCRAS" (H06 lc FR1, according to SEQ ID NO. 23), a light chain framework region FR2 comprising the amino acid sequence "VAWYQQKPGKAPKLLIY" (H06 lc FR2, according to SEQ ID NO. 24), a light chain framework region FR3 comprising the amino acid sequence "SLYSGVPSRFSGSRSGTDFTLTISSLQPEDFATYYC" (H06 lc FR3, according to SEQ ID NO. 25), a light chain framework region FR4 comprising the amino acid sequence "FGQGTKVEIK" (H06 lc FR4, according to SEQ ID NO. 26), a heavy chain framework region FR1 comprising the amino acid sequence "EVQLVESGGGLVQPGGSLRLS-CAAS" (H06 hc FR1, according to SEQ ID NO. 27), a heavy chain framework region FR2 comprising the amino acid sequence "IHWVRQAPGKGLEWVAS" (H06 hc FR2, according to SEQ ID NO. 28), a heavy chain framework region FR3 comprising the amino acid sequence "SYADSVKGRFTISADTSKNTAYLQMNSLRAED-TAVYYC" (H06 hc FR3, according to SEQ ID NO. 29) and a heavy chain framework region 1-R4 comprising the amino acid sequence "WGQGTLVTVSS" H06 he FR4, according to SEQ ID NO. 30).

In yet a preferred embodiment of the present invention, said antibody or IL-38 neutralizing Fab fragment comprises: (a) a light chain comprising SEQ ID NO 1 and (b) heavy chain comprising SEQ ID NO 2 or (a) a light chain comprising SEQ ID NO 3 and (b) heavy chain comprising SEQ ID NO 4.

TABLE 1

Amino acid sequences of the variable chains of Fab E04 and H06

| Identifier | Protein sequence | SEQ ID NO. |
|---|---|---|
| Fab E04 light chain (lc) variable | DIQMTQSPSSLSASVGDRVTITCRASQSYYSYVAWYQQKPGKAPKLLI YSASSLYSGVPSRFSGSRSGTDFTLTISSLQPEDFATYYCQQVFAPITF GQGTKVEIK | 1 |
| Fab E04 heavy chain (hc) variable | EVQLVESGGGLVQPGGSLRLSCAASGFSFSSSSIHWVRQAPGKGLE WVASISPYYSYTSYADSVKGRFTISADTSKNTAYLQMNSLRAEDTAVY YCARTVRGSKKPYFSGWAMDYWGQGTLVTVSS | 2 |
| Fab H06 light chain (lc) variable | DIQMTQSPSSLSASVGDRVTITCRASQSVSSAVAWYQQKPGKAPKLLI YSASSLYSGVPSRFSGSRSGTDFTLTISSLQPEDFATYYCQQAYWSPI TFGQGTKVEIK | 3 |
| Fab H06 heavy chain (hc) variable | EVQLVESGGGLVQPGGSLRLSCAASGFSLSYSYIHWVRQAPGKGLEW VASISPSYSYTSYADSVKGRFTISADTSKNTAYLQMNSLRAEDTAVYYC ARAPVPHVWPYSGFDYWGQGTLVTVSS | 4 |
| Fab E04 lc CDR1 | QSYYSY | 5 |
| Fab E04 lc CDR2 | SAS | — |
| Fab E04 lc CDR3 | QQVFAPIT | 6 |
| Fab E04 hc CDR1 | GFSFSSSS | 7 |
| Fab E04 hc CDR2 | ISPYYSYT | 8 |
| Fab E04 hc CDR3 | ARTVRGSKKPYFSGWAMDY | 9 |
| Fab H06 lc CDR1 | QSVSSA | 10 |
| Fab H06 lc CDR2 | SAS | — |
| Fab H06 lc CDR3 | QQAYWSPIT | 11 |
| Fab H06 hc CDR1 | GFSLSYSY | 12 |

TABLE 1-continued

Amino acid sequences of the variable chains of Fab E04 and H06

| Identifier | Protein sequence | SEQ ID NO. |
|---|---|---|
| Fab H06 hc CDR2 | ISPSYSYT | 13 |
| Fab H06 hc CDR3 | ARAPVPHVWPYSGFDY | 14 |
| Fab E04 lc FR1 | DIQMTQSPSSLSASVGDRVTITCRAS | 15 |
| Fab E04 lc FR2 | VAWYQQKPGKAPKLLIY | 16 |
| Fab E04 lc FR3 | SLYSGVPSRFSGSRSGTDFTLTISSLQPEDFATYYC | 17 |
| Fab E04 lc FR4 | FGQGTKVEIK | 18 |
| Fab E04 hc FR1 | EVQLVESGGGLVQPGGSLRLSCAAS | 19 |
| Fab E04 hc FR2 | IHWVRQAPGKGLEWVAS | 20 |
| Fab E04 hc FR3 | SYADSVKGRFTISADTSKNTAYLQMNSLRAEDTAVYYC | 21 |
| Fab E04 hc FR4 | WGQGTLVTVSS | 22 |
| Fab H06 lc FR1 | DIQMTQSPSSLSASVGDRVTITCRAS | 23 |
| Fab H06 lc FR2 | VAWYQQKPGKAPKLLIY | 24 |
| Fab H06 lc FR3 | SLYSGVPSRFSGSRSGTDFTLTISSLQPEDFATYYC | 25 |
| Fab H06 lc FR4 | FGQGTKVEIK | 26 |
| Fab H06 hc FR1 | EVQLVESGGGLVQPGGSLRLSCAAS | 27 |
| Fab H06 hc FR2 | IHWVRQAPGKGLEWVAS | 28 |
| Fab H06 hc FR3 | SYADSVKGRFTISADTSKNTAYLQMNSLRAEDTAVYYC | 29 |
| Fab H06 hc FR4 | WGQGTLVTVSS | 30 |

It will be understood that the protein or polypeptide sequences referred to above, e.g. in Table 1, may also be represented by a variant sequence, preferably a sequence variant of SEQ ID NO: 1, 2, 3 or 4, which differs therefrom by substitution, addition and/or deletion of one or more amino acids. Preferably, such variant sequences are at least 70%, at least 80%, at least 90%, at least 95% or at least 99% identical over the entire length of the given sequence, preferably of SEQ ID NO. 1, 2, 3 or 4. The term "sequence identity" as used herein refers to a relationship between two or more polypeptide sequence, namely a reference sequence and a given sequence to be compared with the reference sequence. Sequence identity can be determined by comparing the given sequence to the reference sequence after the sequences have been aligned optimally to produce the highest degree of sequence similarity which can be determined by the match between strings of such sequences. Said alignment can be performed by a skilled artisan without further ado. Accordingly, sequence identity provides information on the total number of said matches. Sequence identity can be, preferably, calculated using publicly available computer programs which are known by a skilled artisan, e.g., BLAST and FASTA.

The term "small molecule" as used herein relates to a molecule with a low molecular weight. Typically, a small molecule is an organic compound with a molecular weight of less than 900 daltons. Small molecules include, for example, small secondary metabolites such as alkaloids, lipids, glycosides, terpenes, tetrapyrroles, phenazines, oliogonucleotides and small peptides or peptide-like molecules. The small molecule shall be a direct or indirect inhibitor of IL-38. In a preferred embodiment, the small molecule directly binds to IL-38, thereby inhibiting its activity, for example the interaction of IL-38 with the IL-36 receptor (IL1R6/) and/or IL1RAPL1 and thus blockage of pro-inflammatory downstream signalling.

A "lipid" as used herein relates to hydrophobic or amphiphilic small molecules. Lipids include fatty acids and their derivates such as triglycerides, diglycerides, monoglycerides, phospholipids, lysophospholipids such as lysophosphatidylcholin (LPC), glycerolipids, glycerophospholipids, sphingolipids, saccharolipids, polyketides, prenol lipids and sterol lipids. The lipid shall be a direct or indirect inhibitor of IL-38. Preferably, the lipid directly interacts with the IL-38 protein, thereby inhibiting its activity or it acts as allosteric inhibitor, i.e. by binding to a different site at the IL-36 receptor (IL1R6) and/or the IL-1 receptor accessory protein-like 1 (IL1RAPL1) and thus inhibiting binding of IL-38 to and exerting an antagonistic on said receptors.

The term "inhibitory RNA molecule" as used herein refers to an RNA molecule that inhibits gene expression in a sequence-specific manner. Inhibitory RNA molecules include, for example, small interfering RNA (siRNA), small hairpin RNAs (shRNA) and microRNA (miRNA). The inhibitory RNA molecule typically induces a process known as RNA interference (RNAi), leading to cleavage and/or translational inhibition of a target mRNA with a complementary sequence. It is known to those skilled in the art that the inhibitory RNA molecule can show perfect or imperfect base-pairing to a complementary target sequence. siRNA and shRNAs typically base-pair perfectly and induce mRNA cleavage only in a single, specific target. On the contrary, miRNAs usually have incomplete base pairing to a target and often inhibit the translation of many different mRNAs with similar sequences. An inhibitory RNA molecule may be chemically synthesized or expressed within the cell, for example by introduction of respective recombinant DNA construct. It will be understood that such a DNA construct may contain additional regulatory elements such as an enhancer, a constitutive or inducible promoter or a terminator. The inhibitory RNA molecule shall be a direct or indirect inhibitor of IL-38. In a preferred embodiment, the inhibitory RNA molecule directly interferes with the IL-38 mRNA, impairing translation of IL-38 mRNA into a functional protein and thus inhibiting IL-38 activity.

An "antisense oligonucleotide" as used herein refers to a single strand DNA and/or RNA molecule that is capable of interfering with DNA and/or RNA processing. Antisense oligonucleotides comprise a nucleic acid sequence which is complementary to a specific RNA or DNA sequence. Typically, an antisense oligonucleotide will bind, in a sequence-specific manner, to their respective complementary oligonucleotides, DNA, or RNA, thereby interfering with DNA and/or RNA processing. It is known to those skilled in the art that antisense oligonucleotides may interfere with mRNA processing through RNase H-mediated degradation, translational arrest, modulation of splicing or they may act through steric hindrance of proteins. Means and methods for the design and synthesis of antisense oligonucleotides are well known in the art and include, for example, rational design, chemical modifications and design of antisense oligonucleotides containing locked nucleic acids (LNA) as well as solid-phase chemical synthesis. Antisense oligonucleotides can be chemically synthesized or expressed within the cell, for example by introduction of respective recombinant DNA construct. It will be understood by those skilled in the art that such a DNA construct may contain additional regulatory elements such as an enhancer, a constitutive or inducible promoter or a terminator. Preferably, the antisense oligonucleotide has a length of at least 8, at least 10, at least 12, at least 15, at least 20, at least 25, at least 30, at least 40, at least 45, at least 50 or more nucleotides. The antisense oligonucleotide may comprise deoxyribonucleotides, ribonucleotides, or a combination of both. The antisense oligonucleotide shall be a direct or indirect inhibitor of IL-38. Preferably, the antisense oligonucleotide is a DNA and/or RNA molecule that interferes with expression and/or translation of IL-38, so that a functional IL-38 protein cannot be made.

The term "morpholino" as used herein relates to a molecule that blocks access of other molecules to small, specific sequences of the base-pairing surfaces of a RNA. Typically, said small specific sequences have a length of about 25 nucleotides. In general, a morpholino comprises a backbone of methylenemorpholine rings and phosphorodiamidate linkages. Morpholinos are commonly also known as morpholino oligomers (MO nucleic acid analogs) and phosphorodiamidate morpholino oligomers (PMO). Morpholinos typically do not lead to degradation of their target RNA molecules, but rather act by sterical blocking, i.e. binding to a target sequence within an RNA and thereby getting in the way of molecules that may otherwise interact with said RNA. The morpholino may be a direct or indirect inhibitor of IL-38. Preferably, the morpholio is directly binding to the IL-38 pre-mRNA and/or mRNA and thus interferes with IL-38 translation and/or splicing leading to production of a less or non-functional IL-38 protein. Thus, IL-38 activity is inhibited, e.g. binding of IL-38 to and exerting an antagonistic on the IL-36 receptor (IL1R6) and/or the IL-1 receptor accessory protein-like 1 (IL1RAPL1) is impaired.

The term "deregulation of the tumor-associated immune system" as used herein relates to a modulation of the immune response at the tumor and/or the tumor environment. Preferably, said deregulation is characterized by an increase in anti-tumor immune cell populations and/or an increase of pro-inflammatory cytokines. Further preferred is an inhibition or reactivation of anti-inflammatory or tolerogenic immune cell populations such as regulatory T cells, macrophages and/or myeloid-derived suppressor cells. Anti-tumor immune cell populations, i.e. immune cells that can exert an anti-tumoral activity, are known to those skilled in the art and include, for example, T-cells, NK cells and B-cells. Preferably, the anti-tumor immune cell populations according to the present invention comprise cytotoxic leukocytes such as CD8+ T cells, γδ-T cells, NK cells and/or NKT cells. More preferably, the anti-tumor immune cell populations comprise CD8+ T cells and/or γδ-T cells, most preferably γδ-T cells. In a preferred embodiment of the present invention tumor is breast cancer, i.e. said anti-tumoral activity of pro-inflammatory immune cell populations is directed against breast cancer.

In a preferred embodiment of the present invention, the anti-tumor immune cell population comprises gamma delta T cells (γδ-T cells). γδ-T cells as referred to herein are known to those skilled in the art and describe a subgroup of T cells that may be involved in both innate and adaptive immune responses. In contrast to most T cells that have a T-cell receptor (TCR) composed of two glycoprotein chains, namely the alpha and beta TCR chains, γδ-T cells have a distinctive T-cell receptor on their surface comprising one gamma and one delta chain. Usually, γδ-T cells are less abundant than αβ-T cells. The antigenic molecules that activate γδ-T cells or inhibitory molecules of γδ-T cells are still largely unknown. γδ-T cells seem not to require major-histocompatibility-complex (MHC) presentation of peptide epitopes, although some γδ-T cells were shown to recognize MHC class Ib molecules. Since γδ-T cells can rearrange TCR genes to produce junctional diversity and are able to develop a memory phenotype, they are considered to be part of the adaptive immune system. However, γδ-T cells or certain subsets thereof were also shown to also use their restricted TCR as a pattern recognition receptor and thus may be considered as part of the innate immune system.

According to the present invention, γδ-T cells preferably express the interleukin 1 (IL-1) receptor accessory protein-like 1 (IL1RAPL1) on their surface. IL1RAPL1 is explained elsewhere herein in detail. Preferably, said inhibitor of IL-38 shall prevent the blockage of IL1RAPL1 pro-inflammatory signaling of γδ-T cells caused by IL-38 and thus enable γδ-T cells to secrete pro-inflammatory cytokines and exert an anti-tumor activity.

Pro-inflammatory marker proteins are known to those skilled in the art and include, for example, cytokines such as TNF-α, IL-1β and IL-6. Pro-inflammatory cytokines also include molecules that are known to induce chemotaxis, commonly referred to as chemokines, for example, MCP-1 and MIP-1α. In a preferred embodiment of the present invention, a pro-inflammatory marker signature includes one or more of the following molecules: Interferon-alpha (Ifna), Interferon-beta (Ifnb), Interferon gamma (Ifng), Interleukin 1b (Il1b), Interleukin 36 gamma (Il1f9), Interleukin 21 (Il21), Interleukin 6 (Il6), Interleukin 17 (Il17), Tumor necrosis factor alpha (Tnfa), Interleukin 23 receptor (Il23r), Chemokine (C—C motif) ligand 20 (Ccl20), aryl hydrocarbon receptor (Ahr), perforin 1 (Prf1) and Fas ligand (Fasl). More preferably, one or more of the above mentioned molecules is increased within the tumor, i.e. the intratumoral environment, due to inhibition of IL-38. Further preferred is that inhibition of IL-38 increases interferon gamma (IFN-γ) and/or IL-17 production by γδ T cells and/or CD8+ T cells.

The term "cancer" as used herein relates to a disease that is characterized by an uncontrolled growth of aberrant cells. Cancer includes pre-cancerous states well as a manifested or advanced disease states. The classification of a cancer or tumor stage as well as characteristics and symptoms are known in the art and can, for example, be found in the standard text books of medicine, such as Stedman or Pschyrembl. It is understood by those skilled in the art that cancer cells may migrate from the original tumor site and spread to distant site, also known as dissemination and metastasis formation. Examples of cancers include breast cancer, colorectal cancer, pancreatic cancer, prostate cancer, ovarian cancer, cervical cancer, skin cancer, renal cancer, liver cancer, brain cancer, lymphoma, leukemia and lung cancer. In a preferred embodiment of the present invention the cancer is breast cancer.

The term "treating" as used herein refers to ameliorating or curing a disease or at least one symptom associated therewith. Preferably said disease is cancer, more preferably breast cancer, or at least one symptom associated therewith. Thus, if there is amelioration or cure of the disease or at least a symptom associated therewith, the treatment shall be deemed to be effective. It will be understood that treating might not be effective in all subjects. However, according to the present invention it is envisaged that treatment will be effective in at least a statistically significant portion of subjects to be treated. It is well known to the skilled artisan how to determine a statistically significant portion of subjects that can be effectively treated.

Whether a portion of subjects or any other value referred to herein is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

Preferably, the probability envisaged by the present invention allows that the finding of effective treatment will be correct for at least 60%, at least 70%, at least 80%, or at least 90% of the subjects of a given cohort or population.

The term "preventing" as used herein refers to avoiding the onset of a disease or at least one symptom thereof. Preferably said disease is cancer, more preferably breast cancer. It will be understood by those skilled in the art, that cancer as used herein also includes pre-cancer or pre-malignant states with no or very weak symptoms. It is further known to those skilled in the art that no or very weak symptoms may be present at early stages of cancer and that certain subjects will have an increased risk to develop cancer. For example, subjects having a genetic predisposition, such as a mutation in the BRCA1 and/or BRCA2 gene, are associated with an increased risk to develop cancer, especially breast cancer. Preventive administration of an inhibitor of IL-38 for use according to the present invention is especially useful in patients having an increased risk to suffer from cancer, preferably breast cancer.

The term "subject" as used herein relates to animals, preferably to mammals such as laboratory animals, e.g., mice, rats or monkeys, pets, e.g., dogs, cats or horses, or farming animals, e.g., sheep, goats or cows, and, more preferably, to humans. The terms "subject" and "patient" are used interchangeably herein.

Preferably, the subject is a patient having cancer or subject having an increased risk of developing cancer, especially breast cancer. Subjects with an increased risk of developing cancer include subjects with a familiar history of cancer and subjects having a genetic predisposition for developing cancer such as mutations in the BRCA1 and/or BRCA2 genes. Preferably, said subject or patient is in need of receiving a therapy for cancer, preferably cancer immunotherapy. It is understood that a patient suffering from cancer may have had other treatments before receiving an inhibitor of IL-38 for use according to the present invention and may show symptoms, clinical signs or other parameters related to cancer, preferably to breast cancer.

Typical symptoms of cancer include unexplained weight loss, skin irritation, nausea or vomiting, anemia, jaundice and weakness or fatigue. The most common symptom of breast cancer is a new lump or mass often accompanied by swelling of all or part of a breast, redness, scaliness, or thickening of the nipple or breast skin and breast or nipple pain. Further symptoms and characteristics of cancer, in particular of breast cancer, are well known in the art and are described in the standard text books of medicine, such as Stedman or Pschyrembl.

However, the term also relates to an apparently healthy subject, i.e. a subject not exhibiting any of the aforementioned symptoms, clinical signs or parameters. Especially patients diagnosed at an early stage of cancer and especially breast cancer often appear healthy and do not exhibit any of the aforementioned symptoms. At an early stage, breast cancer is often detected during routine healthcare or regular screening using mammography. Preferably, said apparently healthy subject is a subject with an increases risk of developing cancer, preferably breast cancer, for example a subject with a familiar history of cancer or with a genetic predisposition for developing cancer.

Administration of therapeutic agents to said subject can be done in several ways including parental and/or oral administration. It is known to the skilled artisan, that administration and dosage of a therapeutic agent depends on various factors such as the health state of the subject and the disease to be treated. In a preferred embodiment of the present invention, the inhibitor of IL-38 for use according to the present invention is given to said subject by oral and/or parental administration. In another preferred embodiment, said inhibitor of IL-38 to be administered to the subject is a peptide or protein, a ribozyme, an antibody, a small molecule, a lipid, an inhibitory RNA molecule, an antisense oligonucleotide or a morpholino.

Therapeutic efficacy and toxicity of an inhibitor of IL-38 for use according to the present invention can be determined by standard pharmaceutical procedures, e.g. in experimental animals. For example, the so-called ED50 describes the dose therapeutically effective in 50% of the population and the so-called LD50 describes the dose lethal to 50% of the population. The dose ratio between therapeutic and toxic effects is the therapeutic index, and it can be expressed as the ratio, LD50/ED50. The dosage regimen will be determined by the attending physician and by clinical factors. As is well known in the medical arts, dosages for any one patient depends upon many factors, including the patient's size, age, the particular formulation of the medicament to be administered, sex, time and route of administration, general health, and other drugs being administered concurrently. Progress can be monitored by periodic assessment. Dosage recommendations shall be indicated in the prescribers or users instructions in order to anticipate dose adjustments depending on the considered recipient.

The present invention also contemplates the use of an inhibitor of IL-38 for the manufacture of a medicament for the prevention and/or treatment of cancer.

The present invention also encompasses a pharmaceutical composition comprising an inhibitor of IL-38.

The term "pharmaceutical composition" as used herein refers to mixture comprising an inhibitor IL-38. In a preferred embodiment of the pharmaceutical composition according to the present invention, the inhibitor of IL-38 is a peptide or protein, a ribozyme, an antibody, a small molecule, a lipid, an inhibitory RNA molecule, an antisense oligonucleotide or a morpholino. Moreover, the composition may comprise further components as well such as further therapeutic or auxiliary ingredients and/or pharmaceutically acceptable carriers and/or diluents. Preferably, such further ingredients of the pharmaceutical composition of the invention can be diluents, stabilizing agents, wetting agents, pharmaceutical carriers, additional pharmaceutically active agents, release controlling agents and the like.

In a preferred embodiment of the present invention, the pharmaceutical composition further comprises a pharmaceutically acceptable carrier. A pharmaceutically acceptable carrier according to the present invention must be acceptable in the sense of being compatible with the other ingredients of the formulation and not being deleterious to the recipient thereof. Pharmaceutical carriers may include solid, gel, or liquid carriers such as lactose, terra alba, sucrose, talc, gelatin, agar, pectin, acacia, magnesium stearate, stearic acid, glyceryl mono-stearate or glyceryl distearate. Moreover, further suitable carriers are known in the art and can be found for example in science text books such as Remington's Pharmaceutical Sciences, Mack Publishing Company, Easton, Pa.

Preferably, the pharmaceutical composition of the present invention is to be used as a medicament. Said medicament is, preferably, applied to treat and/or prevent cancer as described elsewhere herein in detail. According to the present invention, the pharmaceutical composition shall, preferably, comprise the inhibitor of IL-38 in a therapeutically effective dose. Therapeutic efficacy and toxicity of an inhibitor of IL-38 can be determined by standard pharmaceutical procedures as describe elsewhere herein. The pharmaceutical composition shall further be adapted for use in treating and/or preventing cancer. Typically, the desired mode of administration will be systemic administration. Thus, the composition of the invention is, preferably, formulated for a systemic application. Preferably, parental administration is done via injection while oral administration is done in the form of tablets, solutions or drinking ampules. Depending on the nature and the mode of action, the composition may also be administered by other routes including dermal, intra-muscular, subcutaneous, oral, intravenous or topical administration. The composition can be formulated for a bolus administration or can be made for continuous applications. Formulations and preparations methods for formulating a composition as a medicament are well known in the art and include, for example, mixing, granulating, compression or dissolving the ingredients as appropriate to form the desired composition. Typically, the therapeutically active ingredients will be mixed and, preferably, combined them with a pharmaceutically acceptable carrier and/or diluent. Moreover, it is known by those skilled in the art that the formulation of a pharmaceutical composition to be used as a medicament shall take place under GMP conditions that will ensure quality, pharmaceutical security, and effectiveness of the medicament.

The definition and explanations given herein above apply mutatis mutandis to the following methods of the present invention.

Encompassed by the present invention is a method for treating and/or preventing cancer in a subject in need thereof comprising administering to said subject an inhibitor of IL-38 in a therapeutically effective amount.

Further encompassed by the present invention is a method for identifying an inhibitor of IL-38 comprising the steps of:
a) contacting a potential inhibitor of IL-38 with γδ-T cells; and
b) determining inhibition of IL-1 receptor accessory protein-like 1 (IL1RAPL1) and/or IL-36 receptor (IL1R6) signaling.

Contacting a potential inhibitor of IL-38 with γδ-T cells is performed in such a way that the compound is potentially capable of partially or fully impairing the activity of IL-38. The method shall preferably be an in vitro method. For example, a potential inhibitor of IL-38, i.e. the substance suspected to inhibit the activity of IL-38, can be applied to the medium or supernatant of γδ-T cells or directly induced or expressed within said γδ-T cells. Characteristics of γδ-T cells are explained elsewhere herein. Moreover, means and methods to isolate, produce and/or culture γδ-T cells are known to those skilled in the art. These include, but are not limited to, separation of γδ-T cells from human blood using magnetic bead-coupled antibodies and magnetic columns, fluorescence-activated cell sorting after marking γδ-T cells with specific antibodies, expansion of γδ-T cells in whole leukocyte preparations with, for example zoledronate or IL-18 (Nussbaumer et al., Essential requirements of zoledronate-induced cytokine and γδ T cell proliferative responses. The Journal of Immunology 191.3 (2013): 1346-1355.2013).

The potential inhibitor of IL-38 can be any compound or substance suspected to be capable of partially or fully impairing the activity of IL-38, e.g. a direct or indirect inhibitor of IL-38 as described elsewhere herein in detail.

Preferably, the potential inhibitor of IL-38 is a peptide or protein, a ribozyme, an antibody, a small molecule, a lipid, an inhibitory RNA molecule, an antisense oligonucleotide or a morpholino as explained elsewhere herein.

Determining inhibition of IL-1 receptor accessory protein-like 1 (IL1RAPL1) and/or IL-36 receptor (IL1R6) signaling, preferably, refers to the measurement of a signal indicative of IL-1 receptor accessory protein-like 1 (IL1RAPL1) and/or IL-36 receptor (IL1R6) activity. As explained above, IL1RAPL1 and IL1R6 are members of the IL-1 receptor family that are characterized by extracellular immunoglobulin(-like) domains and an intracellular TIR domain. Downstream signaling from the activated receptor IL1RAPL1 and/or IL1R6 typically involves the activation of pro-inflammatory signaling pathways, such as NF-κB and mitogen-activated protein kinases (MAPKs), further leading to production and release of pro-inflammatory mediators such as Interferon gamma and Interleukin 17. Receptor antagonists, i.e. molecules that bind to the extracellular domain of IL1RAPL1 and/or IL1R6 and thus block downstream signaling, lead to the production of less pro-inflammatory cytokines. As explained elsewhere herein in detail, IL-38 can bind to IL1RAPL1 and/or IL1R6, thereby blocking pro-inflammatory downstream signaling. An inhibitor of IL-38 would thus release this blockage causing an increase in pro-inflammatory cytokines. Thus, an increased production and/or release of pro-inflammatory cytokines is indicative for an inhibitor of IL-38.

Means and methods to determine inhibition of receptor signaling, such as IL1RAPL1 and/or IL1R6, are known in the art and include, for example, measuring conformational changes of the extracellular and/or intracellular domain(s), binding of molecules to the extracellular domain, recruitment of signaling molecules to the intracellular TIR domain and/or subsequent activation of downstream signaling molecules as described above. Production and/or release of one or more pro-inflammatory cytokines can, for example, be measured by quantitative PCR or ELISA/ELISPOT techniques.

As explained elsewhere herein in detail, a potential inhibitor of IL-38 can be a direct inhibitor, for example an antagonistic antibody that directly binds to IL-38 and thereby blocks its interactions with ILIRAPL1 and/or IL1R6 or it can be an indirect inhibitor of IL-38, e.g. an allosteric inhibitor that directly binds to ILIRAPL1 and/or IL1R6 and thereby allosterically blocks interaction of IL-38 with ILIRAPL1 and/or IL1R6, thus inhibiting the antagonistic activity of IL-38 exerted by binding to ILIRAPL1 and/or IL1R6. Preferably, an inhibitor of IL-38 shall release the blockage on pro-inflammatory signaling mediated by ILIRAPL1 and/or IL1R6. Thus, in case an inhibitor of IL-38 is present, a higher amount of pro-inflammatory cytokines, e.g. an increased amount of IL17, will be produced and released from γδ-T cells, whereas, in case no inhibitor of IL-38 is present, IL-38 will exert its antagonizing effect on ILIRAPL1 and/or IL1R6 leading to less or no production of pro-inflammatory cytokines by γδ-T cells, e.g. less or no IL-17 is present.

Thus, in a preferred embodiment of the present invention an increased production and/or release of at least one pro-inflammatory cytokine by said γδ-T cells shall be indicative for an inhibitor of IL-38. Preferably, said at least one pro-inflammatory cytokine is selected from the group consisting of Interferon-beta, Interferon gamma, Interleukin 6, Tumor necrosis factor alpha (TNFα) and Interleukin 17. Most preferably, said at least one pro-inflammatory cytokine is IL-17.

Advantageously, it has been found in accordance with the studies underlying the present invention that a lack of IL-38 secretion in IL-38 K.O. mice resulted in a significant reduction of breast cancer formation. IL-38 apparently counteracts the immune reaction that will occur during early tumor formation and, thus, supports the development of tumors. Consequently, interfering with said counteraction elicited by IL-38 in, e.g., an IL-38 deficient background or by inhibiting IL-38, results in a reduction of tumor formation due to the fact that the anti-tumor immune reaction can occur. Thanks to the findings underlying the present invention, it is possible to use means for the inhibition of IL-38 as a therapeutic strategy to prevent tumor formation such as formation of breast cancer or any other, preferably, solid, cancer type.

The above explanations and definitions of the terms apply throughout the specification. Moreover, typical embodiments of the inhibitor of IL-38 for use, of the pharmaceutical composition, of the method for treating and/or preventing cancer and of the method for identifying an inhibitor of IL-38 according to the present invention are listed below.

In a preferred embodiment of the inhibitor of IL-38 for use, the inhibitor causes deregulation of the tumor-associated immune system.

In yet a preferred embodiment of the inhibitor of IL-38 for use, the deregulation of the tumor-associated immune system is characterized by an increase in anti-tumor immune cell populations and/or an increase of pro-inflammatory cytokines.

In yet a preferred embodiment of the inhibitor of IL-38 for use, the anti-tumor immune cell population comprises γδ-T cells, wherein said γδ-T cells express the IL-1 receptor accessory protein-like 1 (IL1RAPL1).

In yet a preferred embodiment of the inhibitor of IL-38 for use, the inhibitor prevents interaction of IL-38 and the IL-36 receptor (IL1R6) and/or the IL-1 receptor accessory protein-like 1 (IL1RAPL1).

In yet a preferred embodiment of the inhibitor of IL-38 for use, the inhibitor is a peptide or protein, a ribozyme, an antibody, a small molecule, a lipid, an inhibitory RNA molecule, an antisense oligonucleotide or a morpholino.

In yet a preferred embodiment of the inhibitor of IL-38 for use, the inhibitor is a monoclonal antibody. More preferably, said monoclonal antibody comprises complementarity determining regions (CDRs) as shown in SEQ ID NO: 5, SEQ ID NO: 6, SEQ ID NO: 7, SEQ ID NO: 8, and SEQ ID NO: 9 or CDRs as shown in SEQ ID NO. 10, SEQ ID NO. 11, SEQ ID NO. 12, SEQ ID NO. 13 and SEQ ID NO. 14.

In yet a preferred embodiment of the inhibitor of IL-38 for use, the cancer is breast cancer.

In yet a preferred embodiment of the inhibitor of IL-38 for use, the subject is a mammal, preferably a human.

In yet a preferred embodiment of the inhibitor of IL-38 for use, the inhibitor is given to said subject by parental and/or oral administration.

It will be understood that the present invention also provides a pharmaceutical composition comprising an inhibitor of IL-38.

In a preferred embodiment of the pharmaceutical composition of the present invention, the inhibitor is a peptide or protein, a ribozyme, an antibody, a small molecule, a lipid, an inhibitory RNA molecule, an antisense oligonucleotide or a morpholino.

In yet a preferred embodiment of the pharmaceutical composition of the present invention, the antibody is a monoclonal antibody. More preferably, said monoclonal antibody comprises complementarity determining regions (CDRs) as shown in SEQ ID NO: 5, SEQ ID NO: 6, SEQ ID NO: 7, SEQ ID NO: 8, and SEQ ID NO: 9 or CDRs as shown in SEQ ID NO. 10, SEQ ID NO. 11, SEQ ID NO. 12, SEQ ID NO. 13 and SEQ ID NO. 14.

In a further preferred embodiment of the pharmaceutical composition, the composition further comprises a pharmaceutically acceptable carrier.

In addition, the present invention encompasses an antibody, preferably a monoclonal antibody, comprising complementarity determining regions (CDRs) as shown in SEQ ID NO:

5, SEQ ID NO: 6, SEQ ID NO: 7, SEQ ID NO: 8, and SEQ ID NO: 9 or CDRs as shown in SEQ ID NO. 10, SEQ ID NO. 11, SEQ ID NO. 12, SEQ ID NO. 13 and SEQ ID NO. 14.

Moreover, also encompassed by the present invention is a method for treating and/or preventing cancer in a subject in need thereof comprising administering to said subject an inhibitor of IL-38 in a therapeutically effective amount.

Further encompassed by the present invention is a method for identifying an inhibitor of IL-38 comprising the steps of:
a) contacting a potential inhibitor of IL-38 with γδ-T cells; and
b) determining inhibition of IL-1 receptor accessory protein-like 1 (IL1RAPL1) and/or IL-36 receptor (IL1R6) signaling.

In a preferred embodiment of the method, an increased production and/or release of at least one pro-inflammatory cytokine by said γδ-T cells is indicative for an inhibitor of IL-38. Most preferably, said at least one pro-inflammatory cytokine is IL-17.

All references cited in this specification are herewith incorporated by reference with respect to their entire disclosure content and the disclosure content specifically mentioned in this specification.

FIGURES

FIG. 1: IL-38-deficiency impairs PyMT tumor growth. (A) Tumor diameter and (B) tumor free glands were measured in wildtype (WT) and IL-38 knockout mice (IL-38 KO) in a polyoma middle T oncoprotein (PyMT) mammary carcinoma background (n=22). Data are means±SEM. (C) At week 18 tumors were extracted to calculate the tumor burden in terms of the mice body weight (n=30). (D) The intratumoral levels of IL-38 were measured using Cytometric bead array, and its concentration was correlated with the tumor burden of WT mice n=12. p-values were calculated using (A) Chi square, (B, C) Student's t-test and (D) linear regression.  $p<0.01$, * $p<0.001$.

FIG. 2: Increased percentage of pro-inflammatory and anti-tumoral cell populations in IL-38 KO PyMT tumors. At week 18 PyMT tumors were extracted from wildtype (WT) and IL-38 knockout (IL-38 KO) mice and the immune cell infiltration was determined using multicolor flow cytometry (n=10). Data are means±SEM. p-values were calculated using Student's t-test. * $p<0.05$, ** $p<0.01$.

Figure 3:
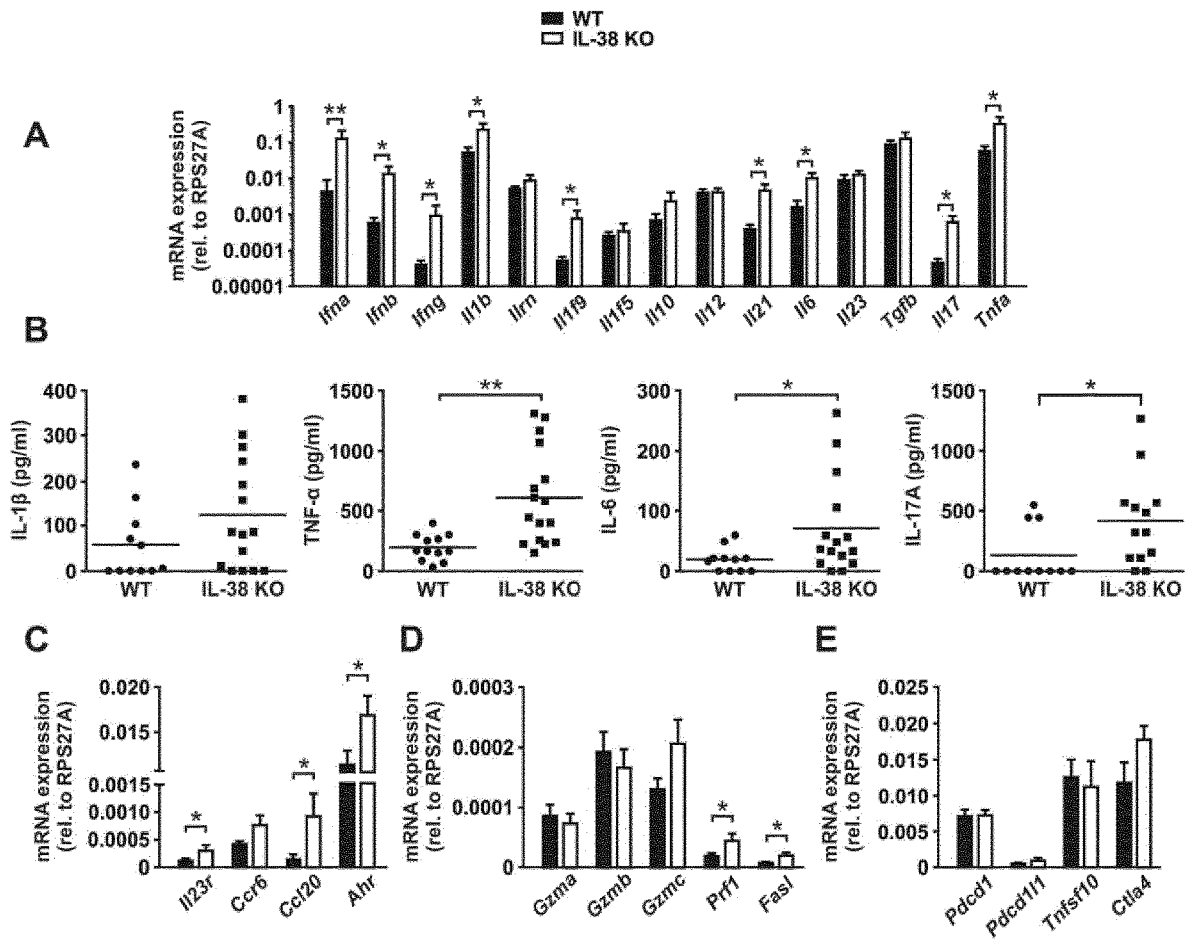
FIG. 3 shows intratumoral pro-inflammatory marker expression is elevated in IL-38 KO tumors. At week 18 PyMT tumors were extracted from wildtype (WT) and IL-38 knockout mice (IL-38 KO) and mRNA expression of (A) a set of cytokines (Protein validation using Cytometric Bead Array in (B)), (C) Th17 markers, (D,E) Cell death and immune checkpoint markers were measured (n=15). Data are means±SEM. p-values were calculated using Student's t-test. * $p<0.05$, ** $p<0.01$.

FIG. 3: Intratumoral pro-inflammatory marker expression is elevated in IL-38 KO tumors. At week 18 PyMT tumors were extracted from wildtype (WT) and IL-38 knockout mice (IL-38 KO) and mRNA expression of (A) a set of cytokines (Protein validation using Cytometric Bead Array in (B)), (C) Th17 markers, (D,E) Cell death and immune checkpoint markers were measured (n=15). Data are means±SEM. p-values were calculated using Student's t-test. * $p<0.05$, ** $p<0.01$.

Figure 4:
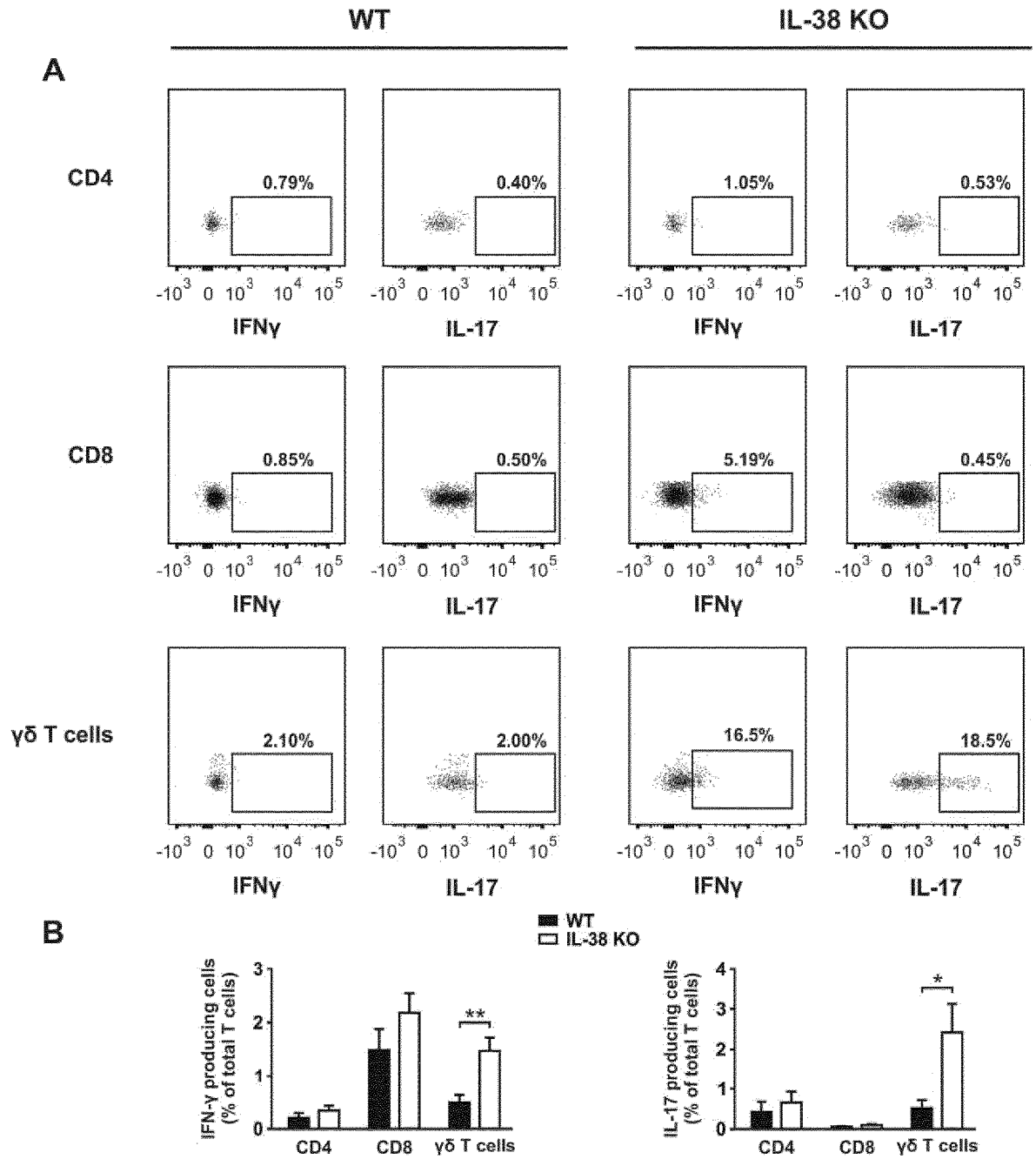
FIG. 4 shows IL-38-deficiency increases IFN-γ and IL-17 production by CD8+ cells and γδ cells respectively. (A) Representative FACS plots and (B) quantification of intracellular staining of IFN-γ and IL-17 by flow cytometry in different T cell populations (n=7). Data are means±SEM. p-values were calculated using Student's t-test. * $p<0.05$, ** $p<0.01$.

FIG. 4: IL-38-deficiency increases IFN-γ and IL-17 production by CD8+ cells and γδ cells respectively. (A) Representative FACS plots and (B) quantification of intracellular staining of IFN-γ and IL-17 by flow cytometry in different T cell populations (n=7). Data are means±SEM. p-values were calculated using Student's t-test. * $p<0.05$, ** $p<0.01$.

FIG. 5: IL-38 directly blocks γδ T cell IL-17 production after TCR stimulus, which increases IL1RAPL1 surface expression. γδ T cells were isolated from spleens and seeded on (A) uncoated and (B) anti-CD3 antibody coated plates. After stimulation with IL-1β (10 ng/ml) and IL-23 (10 ng/ml) in combination with different concentrations (10 ng/ml, 50 ng/ml, 100 ng/ml) of either IL-38, IL-1RA and IL-36RA, IL-17 concentration was measured using Cytometric Beads Array n=10. (C) Representative FACS histogram of the surface expression of IL-1RAPL1 after TCR stimulus (of 6 independent experiments). Data are means±SEM. p-values were calculated using Student's t-test. * $p<0.05$, ** $p<0.01$.

FIG. 6: Amino acid sequences of the variable chains of Fab E04 and H06. Determination of FR (framework region) and CDR (complementarity-determining region) boundaries (given in brackets) and amino acid numbering according to IMGT scheme (www.imgt.org). Asterisks denote additional amino acids in CDR3 of heavy chains. In case of Fab E04 these are positions 111.1, 111.2, 111.3, 112.3, 112.2 and 112.1. In case of Fab H06 these are positions 111.1, 112.2 and 112.1.

Figure 7:
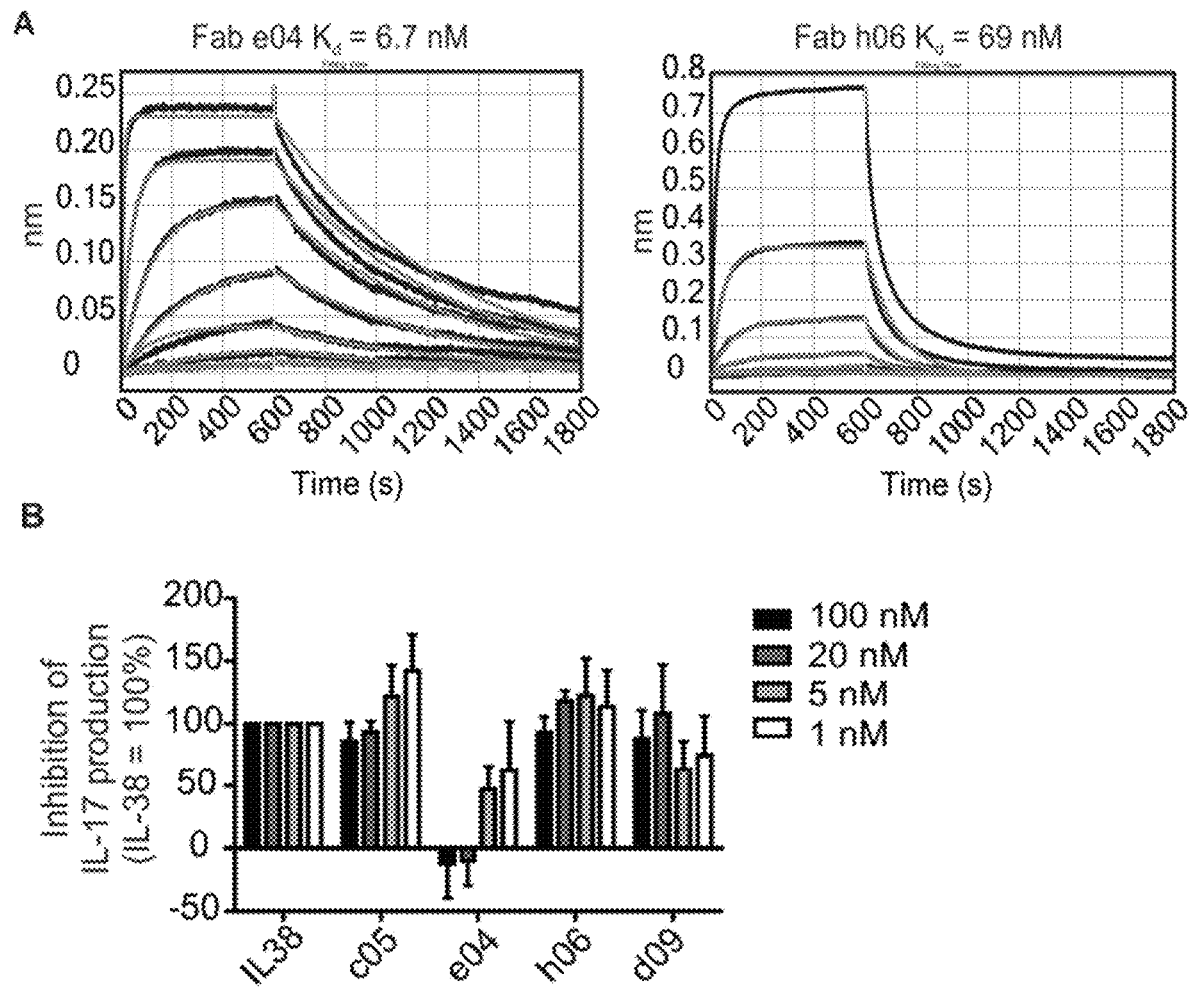
FIG. 7 shows identification of mouse IL-38 neutralizing antibodies. (A) Fitted biolayer interferometry sensograms of 2 selected Fab fragments and their respective Kds. (B) Mouse spleen cells were seeded on anti-CD3 coated plates and treated with IL-1 and IL-23+IL-38 and Fab fragments putatively recognizing murine IL-38. IL-17 levels in supernatants were analyzed after 5 days (n=4). Unrelated Fab fragments c05 and d09 were used as negative controls.

FIG. 7: Identification of mouse IL-38 neutralizing antibodies. (A) Fitted biolayer interferometry sensograms of 2 selected Fab fragments and their respective Kds. (B) Mouse spleen cells were seeded on anti-CD3 coated plates and treated with IL-1 and IL-23+IL-38 and Fab fragments putatively recognizing murine IL-38. IL-17 levels in supernatants were analyzed after 5 days (n=4). Unrelated Fab fragments c05 and d09 were used as negative controls.

EXAMPLES

The invention will be merely illustrated by the following Examples. The said Examples shall, whatsoever, not be construed in a manner limiting the scope of the invention.

Example I: IL-38 Deficiency Results in Less and Smaller Tumors in the MMTV-PyMT Mouse Model MMTV-PyMT transgenic mice express the Polyoma Virus middle T antigen under the mouse mammary tumor virus (MMTV) promoter. These mice spontaneously develop palpable tumors after 6-8 weeks. The number of affected mammary glands and the size/mass of the tumors allow to quantify the outgrowth and the tumor burden, respectively. Using transgenic MMTV-PyMT IL-38 knockout mice, the inventors showed that IL-38 deficiency leads to a decrease in tumor size (FIG. 1A), number of affected mammary glands (FIG. 1B), and tumor burden (FIG. 1C) compared to wildtype (WT) mice. This association of IL-38 deficiency with impaired tumor growth was further analyzed correlating the intratumoral concentration of IL-38 with the tumor burden in the WT mice (FIG. 1D). The IL-38 concentration within the tumor positively correlated with the tumor burden, demonstrating that IL-38 promotes tumor growth and the potential of IL-38 inhibition in anti-tumor therapy.

Example II: Anti-Tumoral Inflammatory Cell Infiltration Increases in IL-38 Deficient Tumors The previously demonstrated anti-inflammatory functions of IL-38 (Mora et al., 2016, Interleukin-38 is released from apoptotic cells to limit inflammatory macrophage responses, J Mol Cell Biol 8: 426-438) suggested an immune-regulatory role of this cytokine also in the tumor microenvironment. First, immune cell infiltration into tumors was therefore analyzed. High immune cell infiltration is an inherent characteristic of solid tumors. It has been widely shown that the immune cell landscape infiltrating the tumor dictates the outcome of cancer patients (Gentles et al., 2015, The prognostic landscape of genes and infiltrating immune cells across human cancers. Nature medicine 21.8: 938-945.). In order to determine whether decreased tumor burden associated with IL-38 deficiency was mediated by changes in the immune cell infiltrate, the tumors of transgenic MMTV-PyMT IL-38 knock-out (KO) and wildtype (WT) mice were analyzed. To compare the immune cell infiltrate, a time point with significant differences in the tumor burden between WT and IL-38 KO mice (week 18) was chosen. IL-38-deficient tumors from IL-38 KO-MMTV-PyMT transgenic mice showed changes in immune cell infiltrations compared to tumors from WT mice (FIG. 2). IL-38 deficiency lead to an increase in the infiltration of total T cells, cytotoxic T cells (CD8+), γδ T cells, NK cells, and NKT cells; all immune cell populations with anti-tumor activity. These results show that IL-38 blockade can be used as a new strategy to manipulate the immune cell landscape within the tumor towards a more inflammatory anti-tumoral microenvironment.

Example III: Increased Tumor Pro-Inflammatory Marker Expression Associated with IL-38 Deficiency The changes in the immune cell infiltration in IL-38-deficient tumors revealed that the absence of this cytokine leads to a more pronounced pro-inflammatory microenvironment. In order to assess the functionality of increased numbers of inflammatory cells the inventors measured the expression levels of pro-inflammatory cytokines (FIG. 3A, B). IL-38-deficient tumors showed higher intratumoral expression of the pro-inflammatory cytokines INF-α, IFN-β, IFN-γ, TNF-α, IL-6, IL-21, IL-10, and IL-17. This increase in the inflammatory milieu is characteristic of an effective anti-tumor immune response. The observed cytokine signature reflects a IL-17-driven inflammatory response. The inventors confirmed this by showing an increase in IL-23R, CCL20, CCR6, and AhR expression (FIG. 3C), which are markers of IL-17-producing cells. As mentioned above, higher pro-inflammatory cytokine expression is a functional validation of increased inflammatory and cytotoxic cells infiltrating the tumor, which mediate an effective anti-tumor immune response. This was supported by the observation of a higher expression of cytotoxic molecules such as Perforin and FasL (FIG. 3D). Interestingly, there were no changes in the expression of the immune checkpoint molecules PD1, PDL 1, and CTLA4 (FIG. 3E), which are the targets of several novel immunotherapy approaches. This indicates that there is likely no compensatory mechanism operating in IL-38 KO tumors mediated by these immune checkpoints, and that the mechanism underlying the effects of IL-38 blockade are independent of the currently used immunotherapy-based treatments. Therefore, IL-38 inhibitors could potentiate/complement the efficacy of immune checkpoint blocking agents.

Example IV: Increased IL-17 Producing γδ Cells and IFN-γ Producing Cytotoxic T Cells in IL-38-Deficient Tumors An increase in IL-17-driven responses might occur differently in the tumor context. On the one hand, IL-17 production by CD4+ cells represents the typical Th17 response, which has a controversial role in tumor immunity. In some models the Th17 axis induces protective immunity whereas in others it increases metastasis and tumor progression (Guery and Hugues, 2015, Th17 Cell Plasticity and Functions in Cancer Immunity. Biomed Res Int. 2015: 314620). On the other hand, IL-17 production by γδ T cells, also known as γδ T17 response, has a clear anti-tumoral role in tumor immunity, directly killing tumor cells, increasing the IFN-γ production by cytotoxic T cells and activating cytotoxic lymphocytes (Santos et al., 2015, γδ T cells in cancer. Nat Rev Immunol 15.11:683-691). Therefore, based on the increased expression of inflammatory markers such as IL-17 and IFN-γ, and the decrease in tumor growth in the IL-38-deficient mice, the inventors hypothesized a γδ T17 response was activated in the absence of IL-38. In order to prove this, intracellular staining of cytokines was performed in immune cells infiltrating WT versus IL-38 KO tumors. The inventors show that production of IL-17 by γδ T cells and IFN-γ by CD8+ cells was increased in IL-38 KO tumor (FIG. 4). These results corroborate an increased protective γδ T17 response, which is induced after depletion of IL-38.

Example V: IL-38 Directly Inhibits γδ T Cells Activated in a TCR-Dependent Manner It was previously shown that IL-38 blocks macrophage IL-6 production and the subsequent IL-17 production by T cells (Mora et al., 2016, Interleukin-38 is released from apoptotic cells to limit inflammatory macrophage responses, J Mol Cell Biol 8: 426-438.). The new findings of an inhibition of the γδ T17 response in the tumor microenvironment raised the question of a putative direct inhibition of γδ T cells by IL-38. The γδ T17 response is activated by IL-1β and IL-23 in a T cell receptor (TCR) dependent or independent manner (Sutton et al., 2009, IL-1 and IL-23 Induce Innate IL-17 Production from γδ T Cells, Amplifying Th17 Responses and Autoimmunity. Immunity 31.2: 331-341.). The inventors therefore sorted γδ T cells from mouse spleens, and induced IL-17 production by treatment with IL-1 and IL-23, with or without anti-CD3 antibodies to mimic TCR activation, in combination with different concentrations of IL-38. Additionally, in order to dissect the mechanism of the IL-38 action on the γδ T cells, the IL-1 family receptor antagonists IL-1RA and IL-36RA were administered. IL-36RA is the antagonist of the IL-36 receptor. It was shown that IL-38 can bind to this receptor (van de Veerdonk et al., 2012, IL-38 binds to the IL-36 receptor and has biological effects on immune cells similar to IL-36 receptor antagonist." Proceedings of the National Academy of Sciences 109.8: 3001-3005), and therefore this antagonist was used in the experiments to investigate a participation of the IL-36 receptor. As shown in FIG. 5, IL-36RA did not affect IL-17 production by γδ T cells, neither in a TCR-dependent nor in a TCR-independent fashion. IL-1RA blocks IL-1β signaling, which was used as stimulus in the experiments. Therefore, as expected, IL-1RA limited both TCR-dependent and -independent γδ T cell activation. Interestingly, IL-38 inhibited exclusively TCR-dependent γδ T cell activation (FIG. 5 A,B). Even though an interaction of IL-38 with IL-1R1 was proposed, which is the receptor that is blocked by the IL-1RA (Lin et al., 2001, Cloning and characterization of IL-1HY2, a novel interleukin-1 family member. Journal of Biological Chemistry 276.23: 20597-20602.), IL-38 did not reproduce the effects of IL-1RA in the TCR-independent activation experiment. IL-38-dependent inhibition of γδ T cell activation only occurred in a TCR-dependent manner, indicating that IL-38 mediated its effect through the interaction with a receptor whose expression is induced after TCR activation. The inventors previously showed that in macrophages the inhibitory effects of IL-38 were mediated through its interaction with the orphan receptor IL-1RAPL1 (Mora et al., 2016, Interleukin-38 is released from apoptotic cells to limit inflammatory macrophage responses, J Mol Cell Biol 8: 426-438.). Indeed, IL-1RAPL1 expression was increased in γδ T cells after TCR activation (FIG. 5C), suggesting that the inhibitory mechanism of IL-38 works through this receptor. These findings support the potential of IL-38 blockade as a therapy to improve protective immunity in the tumor microenvironment. It is important to highlight the advantage that IL-38 inhibition will allow immune activation of TCR-specific responses, and not general systemic immune activation. This could reduce the side effects such as systemic inflammatory responses, which are common with the currently used immunotherapeutic approaches.

Example VI: Generation and Testing of IL-38 Binding Fab Fragments

Over the past decades, Fab (Fragment antigen binding) libraries displayed on filamentous phages have emerged as a powerful alternative to hybridoma methods for the isolation of functional antibodies. In phage display, the antibody fragment is expressed as a fusion with phage coat proteins and presented on the surface of filamentous phages. Each phage particle presents a unique Fab variant and at the same time encapsulates a single stranded plasmid vector that encodes the amino acid sequence of the displayed fragment. The tight physical linkage between the genetic information and the biophysical properties of the displayed protein enables the isolation of an affinity reagent with desired binding properties from an ensemble of phage presenting non-cognate proteins. We generated our own combinatorial Fab library containing about 10^10 different antibody fragments. This library was used for phage selections, using murine IL-38 (bacterially expressed in a C-terminally-biotinylated form) as antigen. Selections resulted in 15 unique Fab fragments that bind with high affinity to murine IL-38. Based on phage IC50 experiments and sequence features in the complementarity-determining regions (CDRs), we have chosen two Fab fragments for expression and validation (amino acid sequences in FIG. 6). The selected antibody fragments showed a ~7 and ~70 nM Kd, as measured by biolayer interferometry (FIG. 7A). We tested these Fab fragments towards their ability to neutralize the IL-17-suppressing effect of IL-38 in the murine system. As indicated in FIG. 7B, an IL-38 neutralizing Fab fragment was identified.

CITED LITERATURE

Gentles et al., 2015, The prognostic landscape of genes and infiltrating immune cells across human cancers. Nature medicine 21.8: 938-945.
Lin et al., 2001, Cloning and characterization of IL-1HY2, a novel interleukin-1 family member. Journal of Biological Chemistry 276.23: 20597-20602.
Mora et al., 2016, Interleukin-38 is released from apoptotic cells to limit inflammatory macrophage responses, J Mol Cell Biol 8: 426-438.
van de Veerdonk et al., 2012, IL-38 binds to the IL-36 receptor and has biological effects on immune cells similar to IL-36 receptor antagonist." Proceedings of the National Academy of Sciences 109.8: 3001-3005.
Nussbaumer et al., 2013, Essential requirements of zoledronate-induced cytokine and γδ T cell proliferative responses. The Journal of Immunology 191.3: 1346-1355.2013
Guéry and Hugues, 2015, Th17 Cell Plasticity and Functions in Cancer Immunity. Biomed Res Int. 2015:314620.
Santos et al., 2015, γδ T cells in cancer. Nat Rev Immunol 15.11:683-691.
Sutton et al., 2009, IL-1 and IL-23 Induce Innate IL-17 Production from γδ T Cells, Amplifying Th17 Responses and Autoimmunity. Immunity 31.2: 331-341.
WO2016/012312 A1

---

What is claimed is:

1. An inhibitor of IL-38 for treating and/or reducing a likelihood of occurrence of cancer in a subject, wherein said inhibitor comprises an antibody comprising complementarity determining regions (CDRs) as shown in SEQ ID NO: 5, SEQ ID NO: 6, SEQ ID NO: 7, SEQ ID NO: 8, and SEQ ID NO: 9 or CDRs as shown in SEQ ID NO: 10, SEQ ID NO: 11, SEQ ID N: 12, SEQ ID NO: 13 and SEQ ID NO: 14, wherein the inhibitor further comprises an amino acid sequence SAS.

2. The inhibitor of IL-38 of claim 1, wherein said antibody is a monoclonal antibody.

3. A pharmaceutical composition comprising an inhibitor of IL-38 according to claim 1.

4. The pharmaceutical composition of claim 3, wherein said antibody is a monoclonal antibody.

5. The pharmaceutical composition of claim 3, further comprising a pharmaceutically acceptable carrier.

6. A method for treating and/or reducing a likelihood of occurrence of cancer in a subject in need thereof comprising administering to said subject an inhibitor of IL-38 according to claim 1 in a therapeutically effective amount.

7. The method of claim 6, wherein said inhibitor causes deregulation of the tumor-associated immune system.

8. The method of claim 7, wherein said deregulation of the tumor-associated immune system is characterized by an increase in anti-tumor immune cell populations and/or an increase of pro-inflammatory cytokines.

9. The method of claim 8, wherein said anti-tumor immune cell population comprises γδ-T cells, wherein said γδ-T cells express the IL-1 receptor accessory protein-like 1 (IL1RAPL1).

10. The method of claim 6, wherein said inhibitor prevents interaction of IL-38 and the IL-36 receptor (IL1R6) and/or the IL-1 receptor accessory protein-like 1 (IL1RAPL1).

11. The method of claim 6, wherein said cancer is breast cancer.

12. The method of claim 6, wherein said subject is a mammal, preferably a human.

13. The method of claim 6, wherein the inhibitor is given to said subject by parental and/or oral administration.

* * * * *

UNITED STATES PATENT AND TRADEMARK OFFICE
CERTIFICATE OF CORRECTION

PATENT NO. : 11,427,630 B2
APPLICATION NO. : 16/612723
DATED : August 30, 2022
INVENTOR(S) : Andreas Weigert et al.

It is certified that error appears in the above-identified patent and that said Letters Patent is hereby corrected as shown below:

On the Title Page

Column 2 Item (56) (Other Publications), Line 27, delete "lnterleukin-1" and insert -- Interleukin-1 --.

Column 2 (Abstract), Line 2-3, delete "can include" and insert -- includes --.

Column 2, Line 8, delete "13 Claims" and insert -- 14 Claims --.

Page 2, Column 2 Item (56) (Other Publications), Line 6, delete "Polsone," and insert -- PLoS One, --.

In the Specification

Column 9, Line 20, delete "rhodamin)," and insert -- rhodamine), --.

Column 12, Line 13 (approx.), delete "1-R4" and insert -- FR4 --.

Column 14, Line 63, delete "oliogonucleotides" and insert -- oligonucleotides --.

Column 15, Line 6-7, delete "lysophosphatidylcholin" and insert -- lysophosphatidylcholine --.

Column 17, Line 27, delete "(Fas1)." and insert -- (Fasl). --.

Column 21, Line 43, delete "ILIRAPL1" and insert -- IL1RAPL1 --.

Column 21, Line 45, delete "ILIRAPL1" and insert -- IL1RAPL1 --.

Column 21, Line 46-47, delete "ILIRAPL1" and insert -- IL1RAPL1 --.

Column 21, Line 48, delete "ILIRAPL1" and insert -- IL1RAPL1 --.

Signed and Sealed this
Tenth Day of January, 2023

*Katherine Kelly Vidal*
Katherine Kelly Vidal
*Director of the United States Patent and Trademark Office*

CERTIFICATE OF CORRECTION (continued)
U.S. Pat. No. 11,427,630 B2

Column 21, Line 50, delete "ILIRAPL1" and insert -- IL1RAPL1 --.

Column 21, Line 55-56, delete "ILIRAPL1" and insert -- IL1RAPL1 --.

Column 23, Line 11-14, delete "5, SEQ ID NO: 6, SEQ ID NO: 7, SEQ ID NO: 8, and SEQ ID NO: 9 or CDRs as shown in SEQ ID NO. 10, SEQ ID NO. 11, SEQ ID NO. 12, SEQ ID NO. 13 and SEQ ID NO. 14." and insert the same on Column 23, Line 10 as a continuation of same paragraph.

Column 25, Line 35, delete "(FIG." and insert -- (FIGS. --.

Column 25, Line 38, delete "IL-10," and insert -- IL-1β, --.

Column 25, Line 52, delete "PDL 1," and insert -- PDL1, --.

Column 26, Line 60, delete "(FIG." and insert -- (FIGS. --.

Column 28, Line 7, delete "–70" and insert -- ~70 --.

Column 28, Line 32, delete "1355.2013" and insert -- 1355.2013. --.

Column 28, Line 40, delete "A1" and insert -- A1. --.

In the Claims

Column 41, Line 23, Claim 1, delete "N:" and insert -- NO: --.

Column 42, Line 33, Claim 12, delete ", preferably a human".

Column 42, after Line 35, insert -- 14. The method of claim 10, wherein the mammal is a human. --.

SEQUENCE LISTING

<160> NUMBER OF SEQ ID NOS: 30

<210> SEQ ID NO 1
<211> LENGTH: 106
<212> TYPE: PRT
<213> ORGANISM: Artificial Sequence
<220> FEATURE:
<223> OTHER INFORMATION: Fab E04 light chain variable

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Tyr Tyr Ser Tyr
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Val Phe Ala Pro Ile Thr

Phe Gly Gln Gly Thr Lys Val Glu Ile Lys
                100                 105

<210> SEQ ID NO 2
<211> LENGTH: 126
<212> TYPE: PRT
<213> ORGANISM: Artificial Sequence
<220> FEATURE:
<223> OTHER INFORMATION: Fab E04 heavy chain variable

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Ser Ile His Trp Val Arg Gln Ala Pro Gly Lys Gly Leu Glu Trp Val
        35                  40                  45

Ala Ser Ile Ser Pro Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Val Arg Gly Ser Lys Lys Pro Tyr Phe Ser Gly Trp Ala
            100                 105                 110

Met Asp Tyr Trp Gly Gln Gly Thr Leu Val Thr Val Ser Ser
        115                 120                 125

<210> SEQ ID NO 3
<211> LENGTH: 107
<212> TYPE: PRT
<213> ORGANISM: Artificial Sequence
<220> FEATURE:
<223> OTHER INFORMATION: Fab H06 light chain variable

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Trp Ser Pro Ile
                85                  90                  95

Thr Phe Gly Gln Gly Thr Lys Val Glu Ile Lys
            100                 105

<210> SEQ ID NO 4
<211> LENGTH: 123
<212> TYPE: PRT
<213> ORGANISM: Artificial Sequence
<220> FEATURE:
<223> OTHER INFORMATION: Fab H06 heavy chain variable

<400> SEQUENCE: 4

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Leu Ser Tyr Ser
            20                  25                  30

Tyr Ile His Trp Val Arg Gln Ala Pro Gly Lys Gly Leu Glu Trp Val
        35                  40                  45

Ala Ser Ile Ser Pro Tyr Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Pro Val Pro His Val Trp Pro Tyr Ser Gly Phe Asp Tyr
                100                 105                 110

Trp Gly Gln Gly Thr Leu Val Thr Val Ser Ser
        115                 120
```

<210> SEQ ID NO 5
<211> LENGTH: 6
<212> TYPE: PRT
<213> ORGANISM: Artificial Sequence
<220> FEATURE:
<223> OTHER INFORMATION: Fab E04 lc CDR1

<400> SEQUENCE: 5

```
Gln Ser Tyr Tyr Ser Tyr
1               5
```

<210> SEQ ID NO 6
<211> LENGTH: 8
<212> TYPE: PRT
<213> ORGANISM: Artificial Sequence
<220> FEATURE:
<223> OTHER INFORMATION: Fab E04 lc CDR3

<400> SEQUENCE: 6

```
Gln Gln Val Phe Ala Pro Ile Thr
1               5
```

<210> SEQ ID NO 7
<211> LENGTH: 8
<212> TYPE: PRT
<213> ORGANISM: Artificial Sequence
<220> FEATURE:
<223> OTHER INFORMATION: Fab E04 hc CDR1

<400> SEQUENCE: 7

```
Gly Phe Ser Phe Ser Ser Ser Ser
1               5
```

<210> SEQ ID NO 8
<211> LENGTH: 8
<212> TYPE: PRT
<213> ORGANISM: Artificial Sequence
<220> FEATURE:
<223> OTHER INFORMATION: Fab E04 hc CDR2

<400> SEQUENCE: 8

```
Ile Ser Pro Tyr Tyr Ser Tyr Thr
1               5
```

<210> SEQ ID NO 9

```
<211> LENGTH: 19
<212> TYPE: PRT
<213> ORGANISM: Artificial Sequence
<220> FEATURE:
<223> OTHER INFORMATION: Fab E04 hc CDR3

<400> SEQUENCE: 9

Ala Arg Thr Val Arg Gly Ser Lys Lys Pro Tyr Phe Ser Gly Trp Ala
1               5                   10                  15

Met Asp Tyr

<210> SEQ ID NO 10
<211> LENGTH: 6
<212> TYPE: PRT
<213> ORGANISM: Artificial Sequence
<220> FEATURE:
<223> OTHER INFORMATION: Fab H06 lc CDR1

<400> SEQUENCE: 10

Gln Ser Val Ser Ser Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Fab H06 lc CDR3

<400> SEQUENCE: 11

Gln Gln Ala Tyr Trp Ser Pro Ile Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Fab H06 hc CDR1

<400> SEQUENCE: 12

Gly Phe Ser Leu Ser Tyr Ser Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Fab H06 hc CDR2

<400> SEQUENCE: 13

Ile Ser Pro Ser Tyr Ser Tyr Thr
1               5

<210> SEQ ID NO 14
<211> LENGTH: 16
<212> TYPE: PRT
<213> ORGANISM: Artificial Sequence
<220> FEATURE:
<223> OTHER INFORMATION: Fab H06 hc CDR3

<400> SEQUENCE: 14

Ala Arg Ala Pro Val Pro His Val Trp Pro Tyr Ser Gly Phe Asp Tyr
1               5                   10                  15
```

-continued

```
<210> SEQ ID NO 15
<211> LENGTH: 26
<212> TYPE: PRT
<213> ORGANISM: Artificial Sequence
<220> FEATURE:
<223> OTHER INFORMATION: Fab E04 lc FR1

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 16
<211> LENGTH: 17
<212> TYPE: PRT
<213> ORGANISM: Artificial Sequence
<220> FEATURE:
<223> OTHER INFORMATION: Fab E04 lc FR2

<400> SEQUENCE: 16

Val Ala Trp Tyr Gln Gln Lys Pro Gly Lys Ala Pro Lys Leu Leu Ile
1               5                   10                  15

Tyr

<210> SEQ ID NO 17
<211> LENGTH: 36
<212> TYPE: PRT
<213> ORGANISM: Artificial Sequence
<220> FEATURE:
<223> OTHER INFORMATION: Fab E04 lc FR3

<400> SEQUENCE: 17

Ser Leu Tyr Ser Gly Val Pro Ser Arg Phe Ser Gly Ser Arg Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 18
<211> LENGTH: 10
<212> TYPE: PRT
<213> ORGANISM: Artificial Sequence
<220> FEATURE:
<223> OTHER INFORMATION: Fab E04 lc FR4

<400> SEQUENCE: 18

Phe Gly Gln Gly Thr Lys Val Glu Ile Lys
1               5                   10

<210> SEQ ID NO 19
<211> LENGTH: 25
<212> TYPE: PRT
<213> ORGANISM: Artificial Sequence
<220> FEATURE:
<223> OTHER INFORMATION: Fab E04 hc FR1

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

```
<210> SEQ ID NO 20
<211> LENGTH: 17
<212> TYPE: PRT
<213> ORGANISM: Artificial Sequence
<220> FEATURE:
<223> OTHER INFORMATION: Fab E04 hc FR2

<400> SEQUENCE: 20

Ile His Trp Val Arg Gln Ala Pro Gly Lys Gly Leu Glu Trp Val Ala
1               5                   10                  15

Ser

<210> SEQ ID NO 21
<211> LENGTH: 38
<212> TYPE: PRT
<213> ORGANISM: Artificial Sequence
<220> FEATURE:
<223> OTHER INFORMATION: Fab E04 hc FR3

<400> SEQUENCE: 21

Ser Tyr Ala Asp Ser Val Lys Gly Arg Phe Thr Ile Ser Ala Asp Thr
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35

<210> SEQ ID NO 22
<211> LENGTH: 11
<212> TYPE: PRT
<213> ORGANISM: Artificial Sequence
<220> FEATURE:
<223> OTHER INFORMATION: Fab E04 hc FR4

<400> SEQUENCE: 22

Trp Gly Gln Gly Thr Leu Val Thr Val Ser Ser
1               5                   10

<210> SEQ ID NO 23
<211> LENGTH: 26
<212> TYPE: PRT
<213> ORGANISM: Artificial Sequence
<220> FEATURE:
<223> OTHER INFORMATION: Fab H06 lc FR1

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 24
<211> LENGTH: 17
<212> TYPE: PRT
<213> ORGANISM: Artificial Sequence
<220> FEATURE:
<223> OTHER INFORMATION: Fab H06 lc FR2

<400> SEQUENCE: 24

Val Ala Trp Tyr Gln Gln Lys Pro Gly Lys Ala Pro Lys Leu Leu Ile
1               5                   10                  15

Tyr

<210> SEQ ID NO 25
```

-continued

```
<211> LENGTH: 36
<212> TYPE: PRT
<213> ORGANISM: Artificial Sequence
<220> FEATURE:
<223> OTHER INFORMATION: Fab H06 lc FR3

<400> SEQUENCE: 25

Ser Leu Tyr Ser Gly Val Pro Ser Arg Phe Ser Gly Ser Arg Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 26
<211> LENGTH: 10
<212> TYPE: PRT
<213> ORGANISM: Artificial Sequence
<220> FEATURE:
<223> OTHER INFORMATION: Fab H06 lc FR4

<400> SEQUENCE: 26

Phe Gly Gln Gly Thr Lys Val Glu Ile Lys
1               5                   10

<210> SEQ ID NO 27
<211> LENGTH: 25
<212> TYPE: PRT
<213> ORGANISM: Artificial Sequence
<220> FEATURE:
<223> OTHER INFORMATION: Fab H06 hc FR1

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 28
<211> LENGTH: 17
<212> TYPE: PRT
<213> ORGANISM: Artificial Sequence
<220> FEATURE:
<223> OTHER INFORMATION: Fab H06 hc FR2

<400> SEQUENCE: 28

Ile His Trp Val Arg Gln Ala Pro Gly Lys Gly Leu Glu Trp Val Ala
1               5                   10                  15

Ser

<210> SEQ ID NO 29
<211> LENGTH: 38
<212> TYPE: PRT
<213> ORGANISM: Artificial Sequence
<220> FEATURE:
<223> OTHER INFORMATION: Fab H06 hc FR3

<400> SEQUENCE: 29

Ser Tyr Ala Asp Ser Val Lys Gly Arg Phe Thr Ile Ser Ala Asp Thr
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35
```

```
<210> SEQ ID NO 30
<211> LENGTH: 11
<212> TYPE: PRT
<213> ORGANISM: Artificial Sequence
<220> FEATURE:
<223> OTHER INFORMATION: Fab H06 hc FR4

<400> SEQUENCE: 30

Trp Gly Gln Gly Thr Leu Val Thr Val Ser Ser
1               5                   10
```